(12) United States Patent
Chang et al.

(10) Patent No.: US 7,790,896 B2
(45) Date of Patent: Sep. 7, 2010

(54) RNA-SELECTIVE PROBES FOR LIVE CELL IMAGING OF NUCLEAR STRUCTURE AND FUNCTION

(75) Inventors: Young-Tae Chang, New York, NY (US); Qian Li, New York, NY (US); Gustavo Rosania, Ann Arbor, MI (US)

(73) Assignee: New York University, New York, NY (US)

( * ) Notice: Subject to any disclaimer, the term of this patent is extended or adjusted under 35 U.S.C. 154(b) by 859 days.

(21) Appl. No.: 11/680,731

(22) Filed: Mar. 1, 2007

(65) Prior Publication Data

US 2008/0064037 A1    Mar. 13, 2008

Related U.S. Application Data

(60) Provisional application No. 60/780,779, filed on Mar. 9, 2006.

(51) Int. Cl.
*C07D 215/38* (2006.01)
(52) U.S. Cl. ...................................... 546/178
(58) Field of Classification Search ................... 546/178
See application file for complete search history.

(56) References Cited

U.S. PATENT DOCUMENTS

2005/0054006 A1    3/2005    Chang et al.
2005/0227293 A1    10/2005    Chang

OTHER PUBLICATIONS

Vurbanova, CA 107:217455, abstract only of Doklady Bolgarskoi Akademii Nauk, vol. 29(12), pp. 62-65, 1986.*

* cited by examiner

*Primary Examiner*—D. Margaret Seaman
(74) *Attorney, Agent, or Firm*—Nixon Peabody LLP

(57) ABSTRACT

The present invention is directed to fluorescent compounds and methods of making said compounds that selectively bind to cellular RNA. The fluorescent compounds of the present invention are useful for live cell imaging applications.

6 Claims, 11 Drawing Sheets

RNA-SELECTIVE PROBES FOR LIVE CELL IMAGING OF NUCLEAR STRUCTURE AND FUNCTION

This application claims the benefit of U.S. Provisional Patent Application Ser. No. 60/780,779, filed Mar. 9, 2006.

The subject matter of this application was made with support from the United States Government under the National Science Foundation, Grant No. CHE-0449139, the National Institutes of Health, Grant No. RO1-GM078200, the National Center for Research Resources/National Institutes of Health, Grant No. C06 RR-16572. The U.S. Government may have certain rights.

FIELD OF THE INVENTION

The present invention is directed to probes for live cell imaging of nuclear structure and function.

BACKGROUND OF THE INVENTION

Live cell imaging using fluorescent microscopy technology has allowed investigation of the transcriptional dynamics of the cell nucleus (Tsien et al., "Seeing the Machinery of Live Cells", *Science* 280:1954-1955 (1998); Stephens et al., "Light Microscopy Techniques for Live Cell Imaging," *Science* 300.82-86 (2003)). RNA molecules in living cells have been successfully visualized using fluorescent labeled RNA microinjection (Mhlanga et al., "tRNA-Linked Molecular Beacons for Imaging mRNAs in the Cytoplasm of Living Cells," *Nucleic Acid Res.* 33: 1902-1912 (2005)), fluorescence in situ hybridization (FISH) (Femino et al., "Visualization of Single RNA Transcripts in Situ," *Science* 280:585-590 (1998); Dirks et al., "Visualizing RNA Molecules Inside the Nucleus of Living Cells," *Methods* 29:51-57 (2003)), or the green fluorescence protein (GFP), or its derivative (YFP), tagged RNA-binding proteins (Andersen et al., "Nucleolar Proteome Dynamics," *Nature* 433:77-83 (2005); Bertrand et al., "Localization of ASH1 mRNA Particles in Living Yeast," *Mol. Cell.* 2:437-445 (1998)). However, the global dynamics of RNA distribution and transcriptional activity in the cell nucleus, in relation to the higher order structural organization of DNA, and the temporal and spatial processing and transportation of RNA molecules remains to be analyzed. To achieve this goal, a cell-permeate, RNA-selective fluorescent probe for staining live cells would be essential.

Small cell permeate fluorescent organic molecules are widely used as probes to study living cells (Johnson, "Fluorescent Probes for Living Cells," *Histochem. J.* 30:123-140 (1998)). Although cell microinjection (Mhlanga et al., "tRNA-Linked Molecular Beacons for Imaging mRNAs in the Cytoplasm of Living Cells," *Nucleic Acid Res.* 33: 1902-1912 (2005)), GFP plasmid transfection (Zhang et al., "Creating New Fluorescent Probes for Cell Biology," *Nat. Rev. Mol. Cell. Bio.* 3:906-918 (2002)), and other methods (McNeil et al., "Glass Beads Load Macromolecules into Living Cells," *J. Cell. Sci.* 88:669-678 (1987)) to introduce probes into cells have their own advantages for specific study, small molecule imaging probes are often the most practical tool for biological imaging research and medical diagnosis. Many fluorescent dyes are commercially available and stain a variety of living cell organelles, such as the nucleus (Martin et al., "DNA Labeling in Living Cells," *Cytometry Part A* 67A:45-52 (2005); Krishan et al., "DAPI Fluorescence in Nuclei Isolated From Tumors," *J. Histochem. Cytochem.* 53:1033-1036 (2005)), mitochondria (Pendergrass et al., "Efficacy of MitoTracker Green and CMXrosamine to Measure Changes in Mitochondrial Membrane Potentials in Living Cells and Tissues," *Cytometry Part A* 61:162-169 (2004)), lysosomes (Rustom et al., "Nanotubular Highways for Intercellular Organelle Transport," *Science* 303:1007-1010 (2004)), and endoplasmic reticulum (Mironov et al., "[$Ca^{2+}$]i Signaling Between Mitochondria and Endoplasmic Reticulum in Neurons is Regulated by Microtubules. From Mitochondrial Permeability Transition Pore to $Ca^{2+}$-induced $Ca^{2+}$ Release," *J. Biol. Chem.* 280:715-721 (2005)). In contrast, RNA-specific dyes for staining live cells are not readily available. SYTO®RNASelect (Invitrogen-Molecular Probes, Carlsbad, Calif.) is the only commercially available dye for live cell RNA-imaging (Haulgland, "The Handbook, A Guide to Fluorescent Probes and Labeling Technologies," tenth ed. M. T. Z. Spence, eds. pp 327, 710-711), but its usefulness has not been widely proven and its molecular structure has not yet been published.

In the past, it has been shown that most nuclear RNA is localized to the nucleolus—a region of the nucleus that is clearly visible using phase contrast microscopy as the densest, phase-dark region of the nucleus. The nucleolus is the key site in the nucleus for synthesis and assembly of ribosomal RNAs (rRNA). Its functions are tightly related to cell growth and proliferation (Lam et al., "The Nucleolus," *J. Cell Sci.* 118:1335-1337 (2005); Olson et al., "Conventional and Non-Conventional Roles of the Nucleolus," *Int. Rev. Cytol.* 219: 199-266 (2002); Carmo-Fonseca et al., "To Be or Not To Be in the Nucleolus," *Nat. Cell Bio.* 2:E107-E112 (2000)). It is known that nucleolar rRNA assembly takes place during late telophase and throughout interphase, and that rRNAs disassemble when cells enter mitosis (Hernandez-Verdun et al., "Emerging Concepts of Nucleolar Assembly," *J. Cell Sci.* 115:2265-2270 (2002)). However, the detail of nucleolar dynamic mechanisms of intracellular distribution, trafficking and localization throughout a complete cell cycle are not known. Since it is hard to study the nucleolar dynamics using pre-fixed cells, a fluorescent, RNA-selective live cell imaging dye would be greatly advantageous in terms of observing changes in RNA content and distribution, in relation to the organization of DNA within the cell nucleus.

Previously, it has been demonstrated that styryl compounds have the potential to be good live cell fluorescent probes (Rosania et al., "Combinatorial Approach to Organelle-Targeted Fluorescent Library Based on the Styryl Scaffold," *J. Am. Chem. Soc.* 125:1130-1131 (2003)), particularly because they have high affinity to DNA (Lee et al., "Development of Novel Cell-Permeable DNA Sensitive Dyes Using Combinatorial Synthesis and Cell Based Screening," *Chem. Comm.* 15:852-1853 (2003)). However, finding RNA-selective compounds for live cell imaging is difficult, because small nucleic acid binding molecules generally have better affinity to double-stranded DNA compared to single-stranded RNA. In addition, the living cell system is complicated by the fact that it is rich in proteins and membranes that may lead to non-specific binding of hydrophobic imaging probes. For imaging applications, the RNA binding compound needs to have high cell plasma and nuclear membrane permeability, be well-tolerated by living cells, and resist photobleaching. The present invention is directed to overcoming these and other deficiencies in the art.

SUMMARY OF THE INVENTION

One aspect of the present invention relates to a first fluorescent compound, referred to as F112, of the formula:

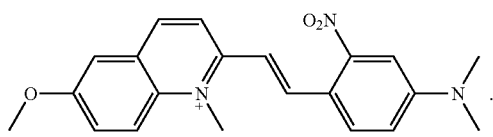

A second aspect of the present invention relates to a process of making the first fluorescent compound having the formula:

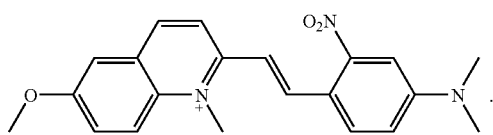

This process comprises the step of reacting an aldehyde having the formula:

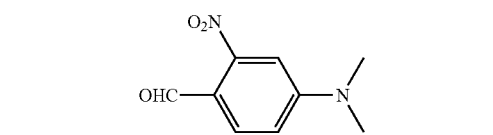

with a methylpyridinium salt of the formula:

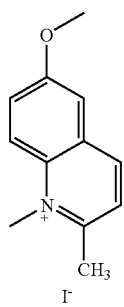

under conditions effective to produce the first fluorescent compound.

A third aspect of the present invention relates to a second fluorescent compound, referred to as E144, having the formula:

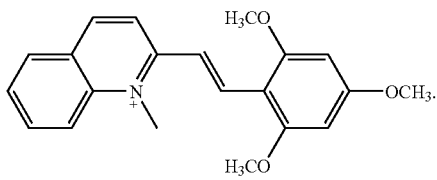

Another aspect of the present invention relates to a process of making the second fluorescent compound having the formula:

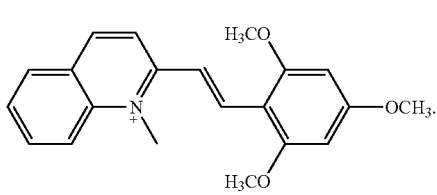

This process comprises the step of reacting an aldehyde having the formula:

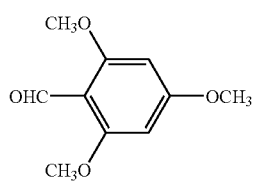

with a methylpyridinium salt of the formula:

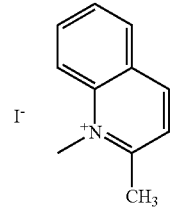

under conditions effective to produce the second fluorescent compound.

Another aspect of the present invention includes a process of making a the third fluorescent compound, referred to as E36, having the formula:

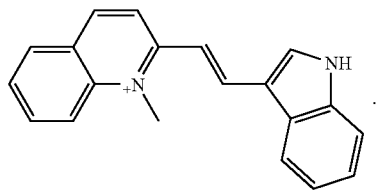

This process comprises the step of reacting an aldehyde having the formula:

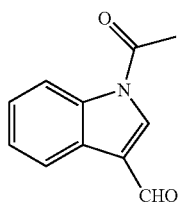

with a methylpyridinium salt of the formula:

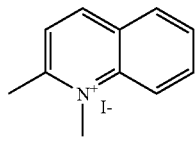

under conditions effective to produce the second fluorescent compounds

Another aspect of the present invention relates to a method of detecting a cellular organelle. This method includes incubating cells in the presence of the first or second fluorescent compounds and detecting fluorescence emissions.

A further aspect of the invention relates to a method of detecting cellular DNA or RNA. This method includes incubating cells in the presence of the first or second fluorescent compounds and detecting fluorescence emissions.

BRIEF DESCRIPTION OF THE DRAWINGS

FIG. 3A shows a dye concentration dependency titration curve. Samples containing 50 µg/mL RNA in TE buffer with an increasing concentration of compound from 0.15 µM to 10 µM. Shown here is the intensity increase recorded at the emission $\lambda_{max}$ wavelength of each dye. FIG. 3B shows a RNA (black line) vs. DNA (light gray line) selectivity titration curve. The samples contain fixed concentration of dyes (E36: 5 µM; E144: 10 µM; F22: 10 µM) in TE buffer with an increasing concentration of RNA or DNA from 0.19 µg/mL to 200 µg/mL. Data points were in duplicated in individual experiments, and error bars represent standard deviation.

In FIG. 5A, A549 and 3T3 cells were incubated with increasing concentrations (5 µM, 10 µM, 13.5 µM, or 20 µM) of each dye (E36: purple bars; E144: green bars; F22: blue bars) for 5, 15, or 24 hours. Cytotoxicity was measured using the MTS assay. The Y axis represents the percentage of cell survival. In FIG. 5B, A549 and 3T3 cells were incubated with 5 µM of RNA-selective compound or 1 µM of Hoechst (E36: purple bars; E144: green bars; F22: blue bars; Hoechst: yellow bars). Cells were then irradiated by proper fluorescent filters (E36 and E144: FITC, F22: Cy3, Hoechst: DAPI) for five minutes followed by a 5 or 24 hour incubation period. Phototoxicity was measured by the MTS assay. The Y-axis represents the percentage of cell survival. Error bars represent standard deviation.

DETAILED DESCRIPTION OF THE INVENTION

Figure 1:
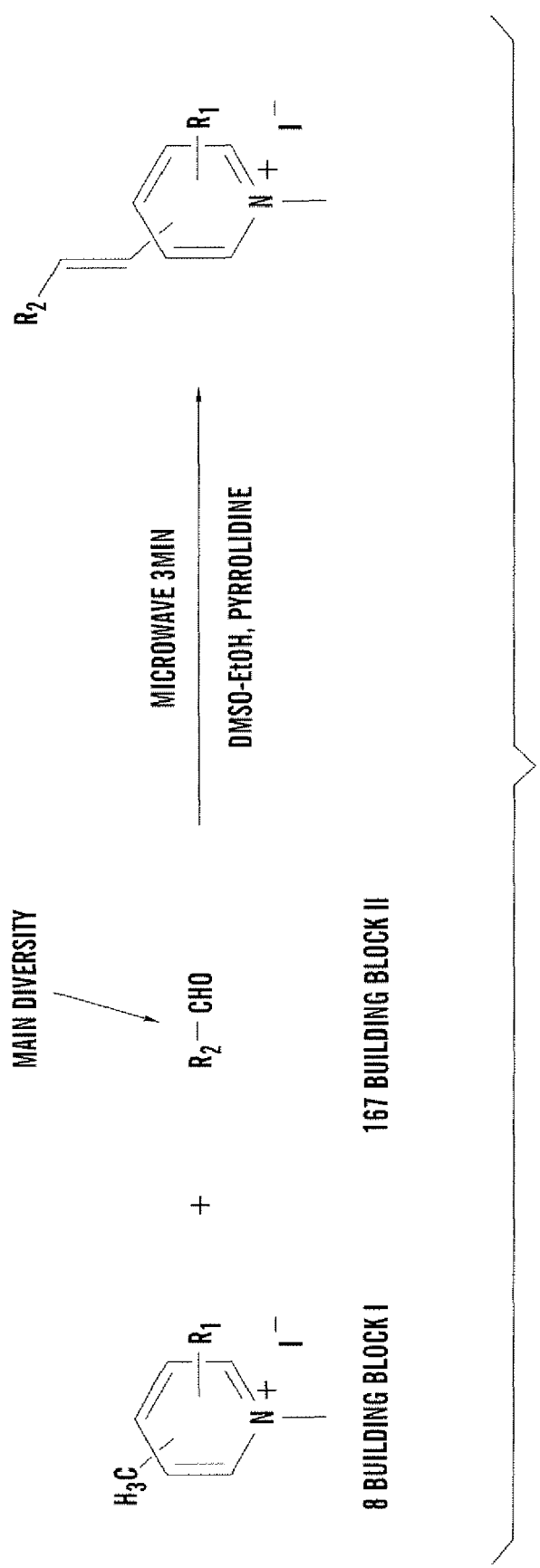
FIG. 1 depicts the general synthetic scheme of styryl compounds.

A first aspect of the present invention relates to a first fluorescent compound, referred to as F112, having the structural formula;

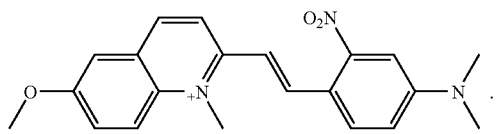

A second aspect of the present invention relates to a process of making the first fluorescent compound having the formula:

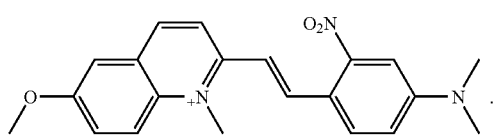

This process comprises the step of reacting an aldehyde having the formula:

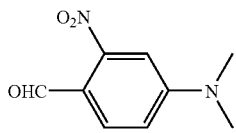

with a methylpyridinium salt of the formula:

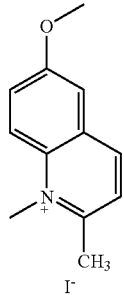

under conditions effective to produce the first fluorescent compound. A related process is described in U.S. Patent Application Publication No. US2005/00540006, which is hereby incorporated by reference in its entirety.

A third aspect of the present invention relates to a second fluorescent compound, referred to as E144, having the formula:

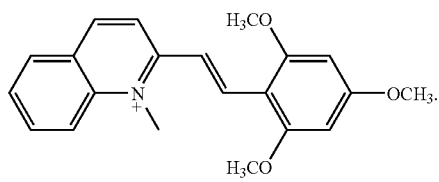

Another aspect of the present invention relates to a process of making the second fluorescent compound having the formula:

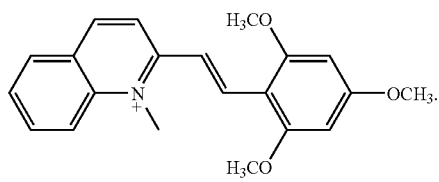

This process comprising the step of reacting an aldehyde having the formula;

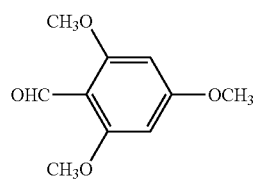

with a methylpyridinium salt of the formula:

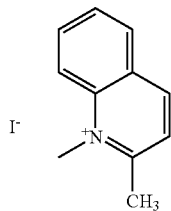

under conditions effective to produce the second fluorescent compound. A related process is described in U.S. Patent Application Publication No. US2005/00540006, which is hereby incorporated by reference in its entirety.

Another aspect of the present invention includes a process of making a the third fluorescent compound, referred to as E36, having the formula:

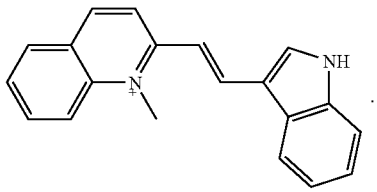

This process comprises the step of reacting an aldehyde having the formula:

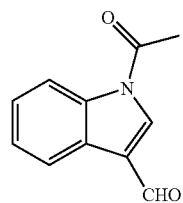

with a methylpyridinium salt of the formula:

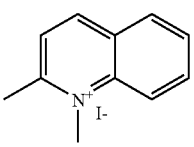

under conditions effective to produce the second fluorescent compound. A related process is described in U.S. Patent Application Publication No. US2005/00540006, which is hereby incorporated by reference in its entirety.

In a preferred embodiment of the present invention, the reaction between the aldehyde and the methylpyridinium salt is carried out in the presence of a secondary amine catalyst, a solvent, such as a mixture of DMSO-ethanol, and with exogenous heat energy. The secondary amine catalyst is exemplified by pyrrolidine or piperidine; however, any secondary amine catalyst can be used. The reaction solvent can be any suitable polar solvent, including but not limited to, dimethylsulfoxide (DMSO), dimethylformamide (DMF), dioxane, water, ethanol, methanol, and ethyl acetate. Exogenous heat energy, such as microwave energy, is applied to the reaction system for about 1 to about 60 minutes to form the styryl-based fluorescent dyes of the present invention. Other forms of energy are also suitable for the synthesis of styryl compounds, including for example, infrared energy.

Another aspect of the present invention relates to a method of detecting a cellular organelle. This method includes incubating cells in the presence of the first or second fluorescent compounds of the present invention and detecting fluorescence emissions. Cellular organelles that can be detected with the compounds of the present invention include nuclear-organelles, mitochondrial organelles, cytosolic organelles, vesicular organelles, granular organelles, nucleolar organelles, and reticular organelles.

A further aspect of the present invention relates to a method of detecting cellular DNA or RNA. This method includes incubating cells in the presence of the first or second fluorescent compounds and detecting fluorescence emissions. In a preferred embodiment of the present invention, the compounds selectively bind to and detect cellular RNA. Biological samples suitable for RNA detection using the compounds of the present invention include any cell or tissue sample containing RNA molecules, including but not limited to, fresh or cultured cells, cell lines, cells in biological fluids, cells in tissue or biopsy, cells grown in suspension, or cells grown in monolayers.

In a preferred embodiment of the present invention, the compounds can be used to detect cellular RNA within live cells or tissue. Live cell imaging of RNA allows for analysis of the global dynamics of RNA distribution, processing, transportation and transcriptional activity within the cell nucleus. Alternatively, the cell or tissue sample can be fixed and permeabilized prior to or after RNA staining with compounds.

In general, the compounds of the present invention can be used without further purification after synthesis. Alternatively, the compounds can be purified via standard filtration techniques known in the art or by thin-layered chromatography or column chromatography techniques also standard in the art. Compounds, in the dry state, can be dissolved in DMSO or other suitable organic water-miscible solvent to obtain a working stock solution. The stock solution can be further diluted in cell culture media or saline solution for direct application to the biological sample.

The concentration of compound most optimal for cellular RNA imaging will vary depending on cell type, density, and morphology. The preferred concentration produces optimum fluorescent brightness per cell with minimal to no non-specific binding of the compound to other cellular constituents. In a preferred embodiment of the present invention, a concentration of 1-20 μM of the RNA dye can be used.

Stock solution of the dye compounds can be diluted using cell media or any physiologically buffered saline solution and applied directly to the biological sample. Sufficient time is allowed for the dye in solution to bind to the intracellular RNA molecules. Typically, less than about thirty minutes is sufficient incubation time for the dye to enter cells and bind to RNA. However, this time can vary based on cell type, density, and morphology. Following incubation, the media containing the dye is aspirated and cells are washed with fresh media or buffered saline solution prior to fluorescence detection.

The compounds of the present invention can be used in conjunction with one or more additional reagents that are separately detectable to allow dual localization of more than one cellular component at one time. The additional reagents may bind other cellular organelles, such as nuclear, mitochondrial, cytosolic, vesicular, granular, nucleolar, or reticular organelles. Alternatively, the additional reagents may bind other cellular constituents such as proteins (i.e. receptors, enzymes) or nucleic acids (i.e. DNA). Preferably, the additional reagent or reagents are also fluorescent having different spectral properties from those of the RNA selective compounds of the present invention. Alternatively, the additional reagents may be detected by some other means commonly known in the art.

Minimal preparation is required for observation of the cells after incubation with the dye compounds of the present invention. Following incubation with media containing the compounds, the media is removed and cells washed one to two times with fresh media or saline solution. Observation can be conducted in live cells maintained in normal cell culture media or any physiological saline solution. Alternatively, cells can be fixed prior to observation. A number of fixatives and fixation conditions are suitable for practicing the present invention. Useful fixatives include, but are not limited to, formaldehyde, paraformaldehyde, formalin, glutaraldehyde, cold methanol, and 3:1 methanol:acetic acid. Typically, cell fixation is accomplished by incubating in a 3.7% solution of paraformaldehyde for about 15-30 minutes.

Cellular fluorescence can be observed using any means for the detection of fluorescent emissions that is known in the art including, but not limited to, fluorometers, fluorescence plate readers, flow cytometers, or fluorescent microscopy.

EXAMPLES

The Examples set forth below are for illustrative purposes only and are not intended to limit, in any way, the scope of the present invention.

Example 1

Materials and Instruments

Unless otherwise noted, chemical materials and solvents were purchased from commercial suppliers (Sigma-Aldrich, St. Louis, Mo. and Acros, Pittsburgh, Pa.) and were used without further purification. RNA (type VI from torula yeast, Sigma) was used for primary screening. RNA, 16S- and 23S-ribosomal from E. coli, (Roche, Indianapolis, Ind.) and DNA from salmon testes (Sigma) were used for dye concentration dependency study. TE buffer (Tris-EDTA sterile solution at pH 7.5, nuclease and protease-free 0.2 μm filtered solution, GE, Piscataway, N.J.) was used in all solution experiments. A Gemini XS fluorescent plate reader was used in obtaining the excitation and emission spectra in the primary screening and titration assay studies. Greiner 96 or 384 well polypropylene black plates were used in the experiments. Full spectra data of the selected three dyes were obtained by Hitachi F-2500 fluorophotometer. Absorbance spectra were measured using SpectraMax Plus[384] absorbance plate reader and Corning 384-well transparent plates. All dye compounds were identified by LC-MS (Agilent Technologies, Santa Clara, Calif.) using a C18 column (4.6×150 mm) with 4 minutes elution using a gradient of 5-95% $CH_3CN$ (containing 1% acetic acid)-$H_2O$ (containing 1% acetic acid), with UV detector at λ=250 nm, 350 nm, 430 nm, 500 nm, and an electrospray ionization source. Bruker Ultrashield 400 MHz NMR was used to obtain spectra of selected compounds. Human Hela cells, A549 human lung carcinoma cells, mice 3T3-L1 cells, and 3T3 fibroblast cells were used in the cell staining study. A Leica confocal DMIRE2 fluorescent microscope was use in the imaging experiments. DAPI (ex 360/40, em 470/40, dichromatic filter 400), FITC (ex 480/40, em 527/30, dichromatic filter 505) and Cy3 (ex 545/30, em 610/75, dichromatic filter 565) band pass filter cubes (Chroma, Rockingham, Vt.) were used for routine cell biological fluorescence imaging applications.

Example 2

General Procedure for Synthesis of Building Block I

The pyridine derivative (2.04 mmol) and iodomethane (2.14 mmol) in ethyl acetate were refluxed overnight. After it was cooled to room temperature, the crystallized methylated products were filtered and washed with ethyl acetate three times and dried in vacuum.

Example 3

General Procedure for Synthesis of Styryl Dye Library

Building blocks I and II were dissolved separately in absolute ethanol (100 mM) as stock solutions. In 96-well Gemini polypropylene microtiter plates, mM of each reactant, 30 µL DMSO, and 0.1 µL pyrrolidine were added using a multipipette. The condensation reaction was carried out in an 800 watt microwave, three minutes for each plate. Product yield and purity were identified by LCMS.

Example 4

General Procedure for Synthesis and Purification of Selected 88 Dye Compounds To a 20 mL vial, building block I (0.1 mmol) and II (0.3-0.5 mmol) was dissolved together in 10 mL absolute ethanol. 3 µL pyrrolidine was added to the solution. The condensation reaction was carried out using a heating block at 80° C. for 3 to 6 hours. After the reaction was completed, the mixture stood at room temperature overnight. Purification was carried out by two different methods depending on the compounds. For the crystallized compounds, the crystal was filtered and re-crystallized in ethanol and dried in vacuum. Non-crystallized compounds were purified by silica preparative TLC or column chromatography using methanol:methylene chloride=1:10. (Solvent gradient polarity might be different depending on compounds). All purified compounds were identified by LCMS and an average of 95% purity was determined in 250 nm absorption wavelength. Note that compound E36 was the deacetylated indole product. The structure and purity of the final selected four compounds were confirmed by $^1$H NMR (400 MHz, Methyl-d3 alcohol-d and Chloroform-d) before detailed cell staining study (Table 1).

TABLE 1

Selected Dyes Purification Method and Characterization

| Dye | Purification Method | Characterization |
|---|---|---|
| E36 | Deacetylated product purified by ethanol re-crystallization | 8.64 (d, J = 8.8 Hz, 1H); 8.49 (d, J = 15.2 Hz, 1H); 8.40 (d, J = 8.8 Hz, 1H); 8.30 (d, J = 8.8 Hz, 1H); 8.15 (d, J = 8.0 Hz, 1H); 8.10 (m, 3H); 7.84 (t, J = 8.0 Hz, 1H); 7.56 (m, 1H); 7.52 (d, J = 15.6 Hz, 1H); 7.39 (m, 2H); 4.52 (s, 3H). LCMS (ESI) m/z for $C_{20}H_{17}N_2^+$ calcd 285.1 found 285.2 |
| E144 | Ethanol re-crystallization. | 8.75 (d, J = 9.2 Hz, 1H); 8.40 (d, J = 15.6 Hz, 1H); 8.35 (d, J = 8.8 Hz, 1H); 8.27 (d, J = 8.8 Hz, 1H); 8.21 (dd, J = 1.2, 8.0 Hz, 1H); 8.14 (ddd, J = 0.8, 7.2, 8.8 Hz, 1H); 8.05 (d, J = 16 Hz 1H); 7.88 (dt, J = 0.4 Hz, 7.6 Hz, 1H); 6.31 (s, 2H); 4.49 (s, 3H); 4.04 (s, 6H); 3.95 (s, 3H). LCMS (ESI) m/z for $C_{21}H_{22}NO_3^+$ calcd 336.2 found 336.2 |
| F22 | Ethanol re-crystallization | 8.53 (d, J = 8.8 Hz, 1H); 8.25 (d, J = 9.2 Hz, 1H); 8.16 (d, J = 9.6, 1H); 7.85 (d, J = 15.2 Hz, 1H); 7.79 (d, J = 8.8 Hz, 1H); 7.60 (dd, J = 2.8, 9.6 Hz, 1H); 7.49 (d, J = 15.6 Hz, 1H); 7.36 (d, J = 2.8 Hz, 1H); 6.70 (d, J = 9.2 Hz, 1H); 4.64 (s, 3H); 4.00 (s, 3H); 3.09 (s, 6H). LCMS (ESI) m/z for $C_{21}H_{23}N_2O^+$ calcd 319.2 found 319.2 |
| F112 | Ethanol re-crystallization | 8.665 (d, J = 8.8 Hz, 1H); 8.494 (d, J = 8.8 Hz, 1H); 8.219 (d, J = 9.6 Hz, 1H); 8.188 (d, J = 15.6 Hz, 1H); 8.066 (d, J = 15.6 Hz, 1H); 8.043 (d, J = 9.2 Hz, 1H); 7.714 (dd, J = 2.8, 9.6 Hz, 1H); 7.347 (d, J = 2.8 Hz, 1H); 7.184 (d, J = 2.4 Hz, 1H); 7.091 (dd, J = 2.8, 9.2 Hz, 1H); 4.866 (s, 3H); 4.032 (s, 3H); 3.150 (s, 6H). LCMS (ESI) m/z for $C_{21}H_{22}N_3O_3^+$ calcd 365.2 found 365.1 |

Example 5

General Fluorescence and Absorbance Spectra Measurement

The fluorescence spectra data in the primary screening and selected dyes titration assay study was obtained by Gemini XS plate reader. RNA solution was prepared right before the assay experiments to avoid possible degradation and contamination. In the primary screening, 1 mg/mL RNA (type VI from torula yeast) buffer solution was used. Point scans were carried out first using five Ex/Em point sets (350 1450, 400/500, 450/550, 500/600, 550/650 nm). Spectra scans were then carried out for the selected dyes. Excitation wavelengths were set at 350 nm, 400 nm, 450 nm, 500 nm, and 550 nm and the emission wavelengths were scanned. RNA (16S- and 23S-ribosomal from *E. coli*) and DNA (salmon testes) titration experiments and quantum yield/extinction coefficient determination for the three best dyes were carried out by the plate reader as well. Excitation $\lambda_{max}$ obtained from F-2500 Hitachi Fluorophotometer was used. Absorbance wavelength was determined by SpectraMax Plus[384] absorbance plate reader. Rhodamine 60 was chosen as standard and 480 nm was used as excitation wavelength in the scanning for quantum yield determination.

Example 6

General Fluorescence Spectra Measurement Using F-2500 Hitachi Fluorophotometer Final concentrations of 5 µM selected dye and 200 µg/mL of RNA in TE buffer were used in the experiments. Generally, the $\lambda_{max}$ (nm) of emission was determined by scanning a fixed excitation first, and the $\mu_{max}$ (nm) of excitation was determined by scanning emission spectrum with a fixed $\mu_{em}$ (nm).

Example 7

Cell Culture Conditions

Hela, 3T3 fibroblast, and 3T3-L1 cells were grown on cell culture Petri dishes in Dulbecco's Modified Eagle Medium (Sigma) with 10% newborn calf serum plus 5 mM L-glutamine and 5 μg/mL gentamicin. A549 cells were grown in Ham's F12 medium with 10% newborn calf serum plus 5 mM L-glutamine and 5 μg/mL gentamicin. Cell cultures were maintained in an incubator at 37° C. in 5% $CO_2$. Cells were cultured in a glass bottom 96-well black plate for imaging 12 to 24 hours prior to experiments.

Example 8

Live Cell Staining

All cell staining imaging followed the same procedure. Generally, dyes in dry state were first dissolved in DMSO to obtain the stock solution. The stock solutions were then added directly to the cell culture wells to reach the desired concentration. Total DMSO was lower than 0.1%. After adding dyes, cells were incubated at 37° C. in 5% $CO_2$ for 25 minutes. The medium was then removed and cells were rinsed with fresh medium twice. The cells were then imaged at ambient temperature in the medium. Exposure time was kept less than 5 seconds and adjusted to each dye.

Example 9

Cytotoxicity Test

Dye DMSO stock solutions were diluted by fresh medium into four desired concentrations (200 μM, 13.5 μM, 10 μM and 5 μM). Cells were cultured in 96-well plate for 12 hours before experiments. The cell medium was then exchanged with different concentrations of dye medium solutions. Cells were incubated at 37° C. in 5% $CO_2$ for 5, 15, or 24 hours before viability by MTS assay was measured. As for the MTS assay, briefly, 3-(4,5-dimethylthiazol-2-yl)-5-(3-carboxymethoxyphenyl)-2-(4-sulfophenyl)-2H-tetrazolium (MTS) and phenazine methosulfate (PMS) were mixed at a ratio of 20:1 right before the experiments. The cell dye medium solution was exchanged with 80 μL of fresh medium followed by the addition of 20 μL MTS/PMS solution to each well. 100 μM hydrogen peroxide was used as positive control. The cell plates were then incubated at 37° C. in 5% $CO_2$ for 2 hours. Absorbance was measured at 490 nm. The absorbance measured for an untreated cell population under the same experimental conditions was used as the reference point to establish 100% cell viability. Duplicated experiments have been tested.

Example 10

Phototoxicity Test

Dye DMSO stock solutions were diluted by fresh medium into working concentration (5 μM). Cells were cultured in 96-well plate for 12 hours before experiments. The cell medium was exchanged with dye medium solutions. Cells were then incubated in at 37° C., in 5% $CO_2$ for 25 minutes before being irradiated by fluorescent light using the appropriate working filter (FITC for E36 and E144; Cy3 for F22) for 5 minutes. The plates were then incubated at 37° C. in 5% $CO_2$ The cell viability was measured by MTS assay after 5 and 24 hours following the cytotoxicity measurement procedure. Duplicated experiments have been tested.

Example 11

DNase and RNase Digest Test

Cells were first fixed using cold (−4° C.) pure methanol for 1 minute at ambient temperature. The cell membrane was then permeabilized by immersion in 1% Triton X-100 for 2 minutes. After rinsing with PBS twice, 100 μL of 50 μM dye PBS solution was added to three adjacent wells. Cells were then incubated in this dye PBS solution for 15 minutes in ambient temperature before being rinsed with clean PBS twice. 100 μL clean PBS (as control experiment), 30 μg/mL DNase (Sigma), or 25 μg/mL DNase-Free RNase (GE) was added to the three adjacent wells and incubated at 37° C. in 5% $CO_2$ for 2 hours. Cells were rinsed with clean PBS twice before imaging. For each dye test, the fluorescent images were obtained using equal exposure time for control, DNase and RNase experiments. DAPI (10 μM) in PBS and SYTO®RNASelect (5 μM) in PBS solution were used for dual staining experiments. Duplicate experiments have been tested.

Example 12

Live Cell Counterstain with Hoechst/DAPI

Cells were first stained in desired concentration following the staining procedure described above. After rinsing with fresh pre-warmed medium, Hoechst stock solution was added to the medium to obtain 1 μM final concentration. Cells were then incubated at 37° C. in 5% $CO_2$ again for 10 minutes and imaged at ambient temperature in the medium. The imaging of DAPI counterstain followed the similar procedure. The final concentration of DAPI was 5 μM. Prior to imaging, the cells were rinsed by fresh medium twice after 20 minutes incubation with DAPI.

Example 13

Synthesis and Characterization of Styryl Dye Library

A new styryl dye library (1,336 members) was prepared for current study. The synthesis followed the procedure developed previously with slight modification (Rosania et al., "Combinatorial Approach to Organelle-Targeted Fluorescent Library Based on the Styryl Scaffold," *J. Am. Chem. Soc.* 125:1130-1131 (2003); U.S. Patent Application No. US2005/0054006 to Chang et al.; which are hereby incorporated by reference in their entirety) (FIG. 1). Compared to the previous styryl dye library, this library has greatly expanded structural diversity due to the use of additional aldehydes as building block II (167 total, Table 2; 41 aldehydes were used in the previous study). All of the aldehydes were commercially available. A huge variety of functional groups were included such as higher conjugation, electron withdrawing and donating groups, acidic and basic groups, multiple functional groups, heterocyclic structures, even polyaromatic structures. The condensation reactions were accelerated by microwave irradiation for three minutes catalyzed by pyrrolidine. The identity and purity of the products were characterized by LCMS, and most reactions produced over 50% yields. More than 80% of products showed strong fluorescence when tested in methanol, which allowed for direct use in the primary screening assays without purification.

TABLE 2
The Styryl Dye Library Decoding Table
Building block I
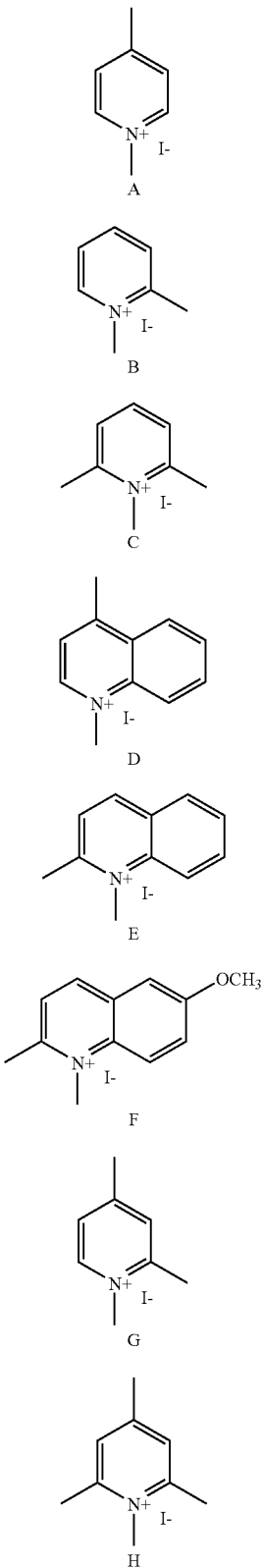
TABLE 2-continued
The Styryl Dye Library Decoding Table
Building block II
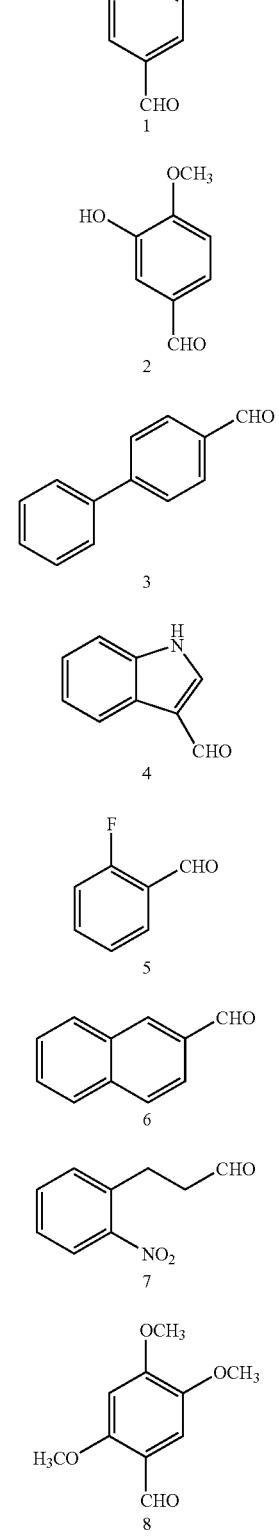

TABLE 2-continued
The Styryl Dye Library Decoding Table
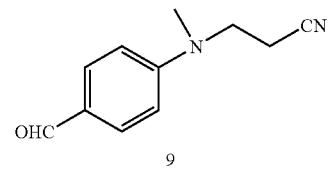
9
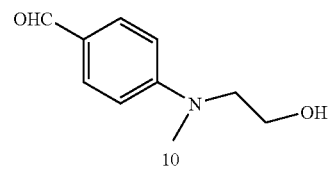
10
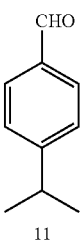
11
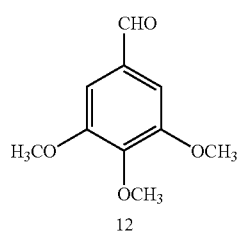
12
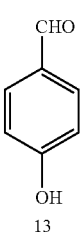
13
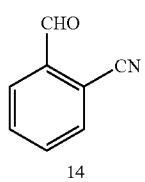
14
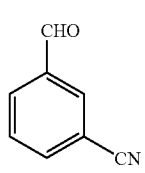
15
TABLE 2-continued
The Styryl Dye Library Decoding Table
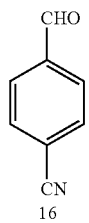
16
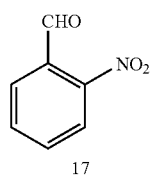
17
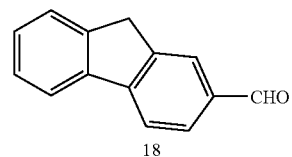
18
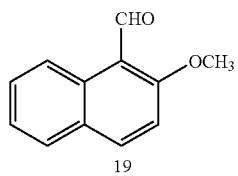
19
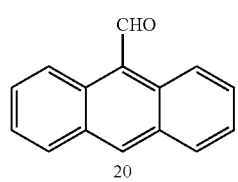
20
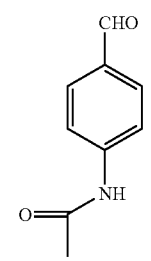
21
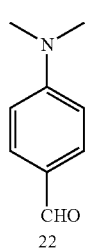
22

TABLE 2-continued
The Styryl Dye Library Decoding Table
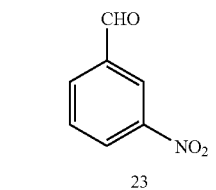
23
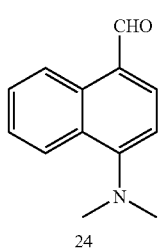
24
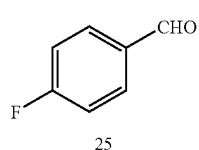
25
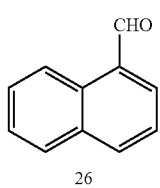
26
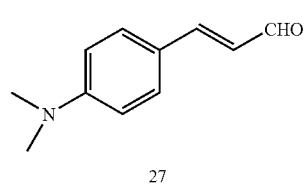
27
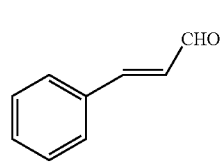
28
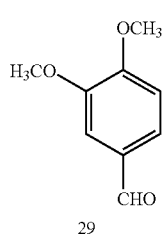
29
TABLE 2-continued
The Styryl Dye Library Decoding Table
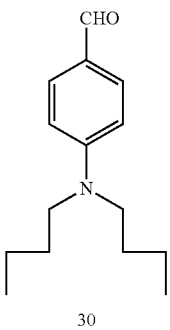
30
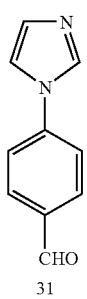
31
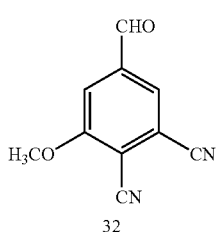
32
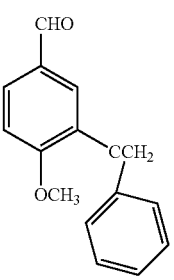
33
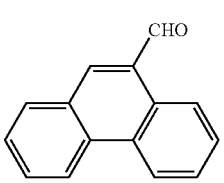
34

TABLE 2-continued
The Styryl Dye Library Decoding Table
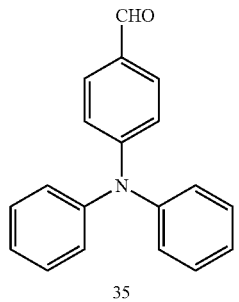
35
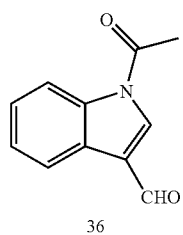
36
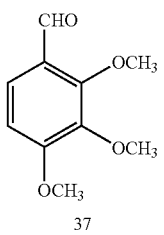
37
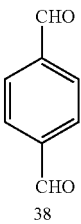
38
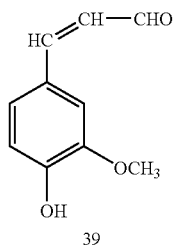
39
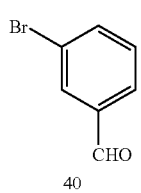
40
TABLE 2-continued
The Styryl Dye Library Decoding Table
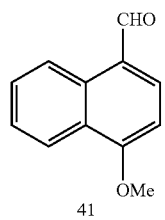
41
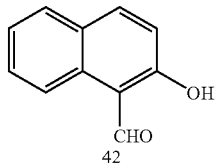
42
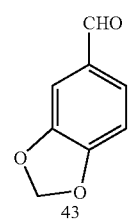
43
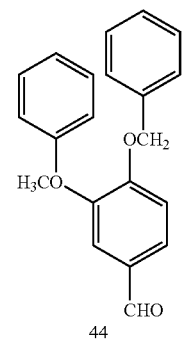
44
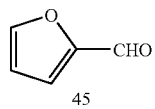
45
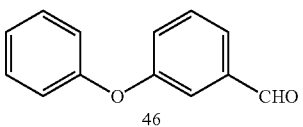
46
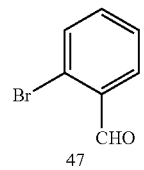
47
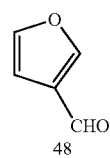
48

TABLE 2-continued
The Styryl Dye Library Decoding Table
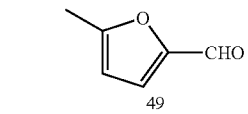
49
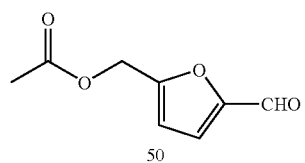
50
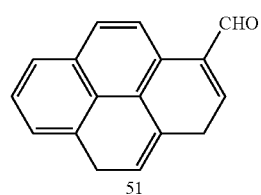
51
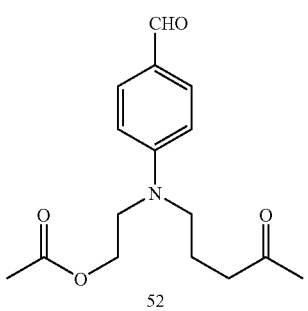
52
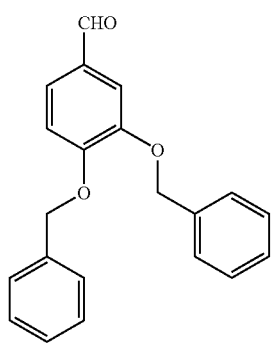
53
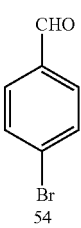
54
TABLE 2-continued
The Styryl Dye Library Decoding Table
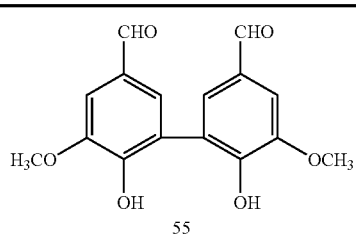
55
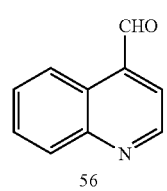
56
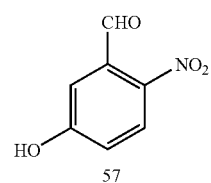
57
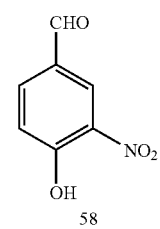
58
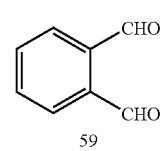
59
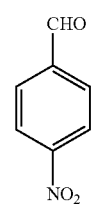
60
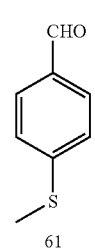
61

TABLE 2-continued
The Styryl Dye Library Decoding Table
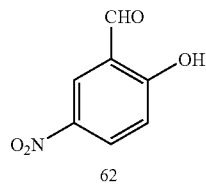
62
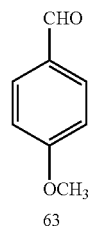
63
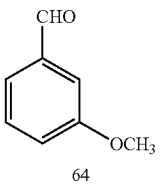
64
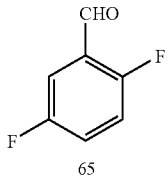
65
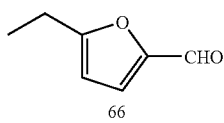
66
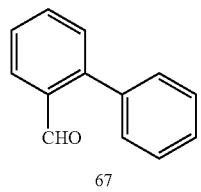
67
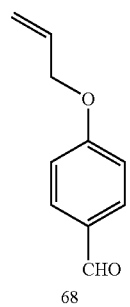
68
TABLE 2-continued
The Styryl Dye Library Decoding Table
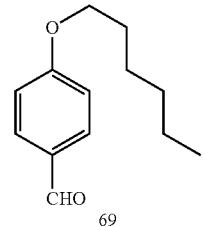
69
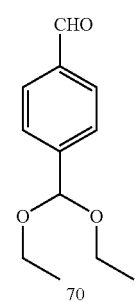
70
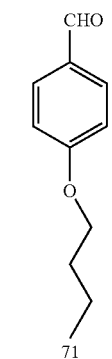
71
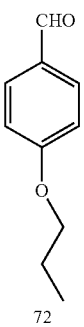
72
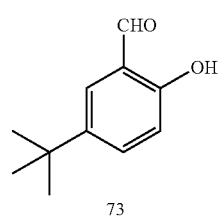
73

TABLE 2-continued
The Styryl Dye Library Decoding Table
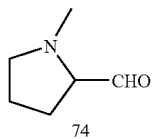
74
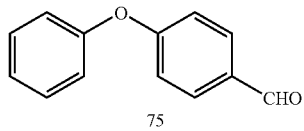
75
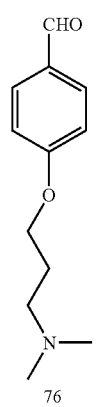
76
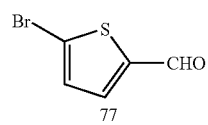
77
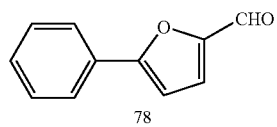
78
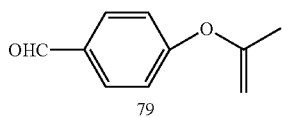
79
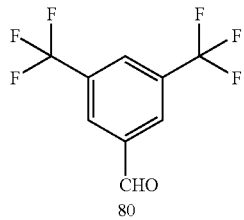
80
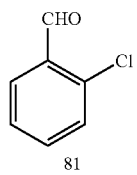
81
TABLE 2-continued
The Styryl Dye Library Decoding Table
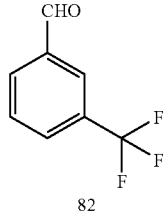
82
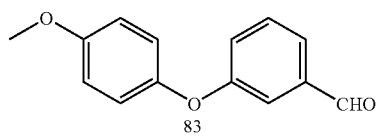
83
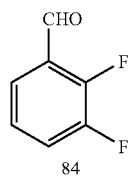
84
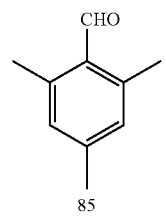
85
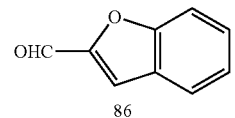
86
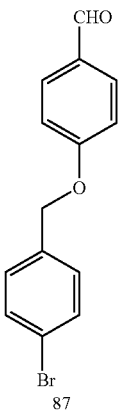
87
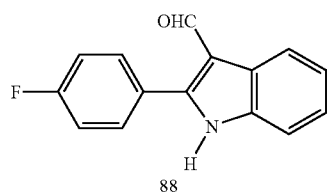
88

TABLE 2-continued

The Styryl Dye Library Decoding Table

89: benzo[1,3]dioxole-4-carbaldehyde

90: 4-tert-butylbenzaldehyde

91: 4-(1,1,2,2-tetrafluoroethoxy)benzaldehyde

92: 4-(diethylamino)benzaldehyde

93: 2,6-dichlorobenzaldehyde

94: 5-chloro-2-hydroxybenzaldehyde

95: 2-bromo-4-hydroxy-5-methoxybenzaldehyde

96: 2,4-dichlorobenzaldehyde

97: 3-(2-methoxyphenyl)acrolein

98: benzo[1,3]dioxole-5-carbaldehyde

99: 8-hydroxyquinoline-2-carbaldehyde

100: 2-benzylidene-octanal

101: 2-benzylidene-heptanal

102: 2,5-dimethoxybenzaldehyde

103: 2,4-dimethoxybenzaldehyde

104: 3-ethoxy-2-hydroxybenzaldehyde

TABLE 2-continued
The Styryl Dye Library Decoding Table
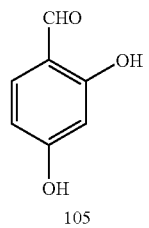
105
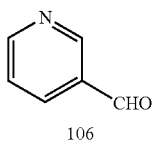
106
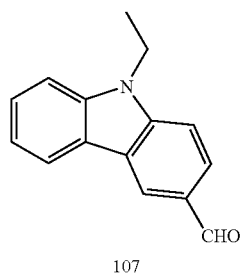
107
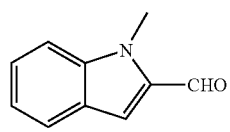
108
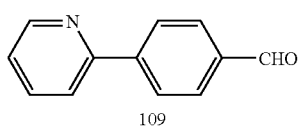
109
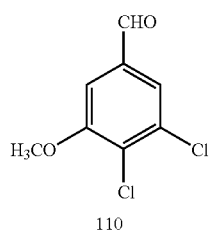
110
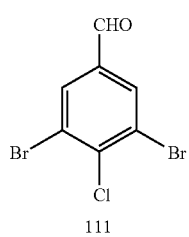
111
TABLE 2-continued
The Styryl Dye Library Decoding Table
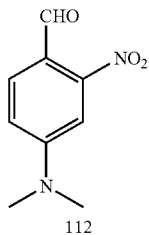
112
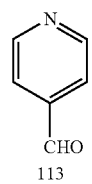
113
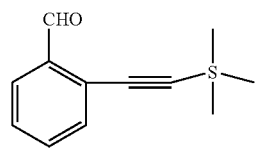
114
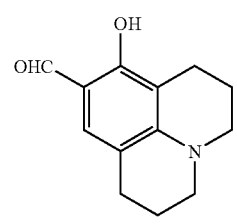
115
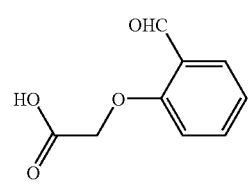
116
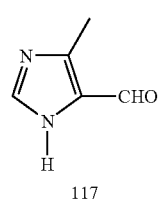
117
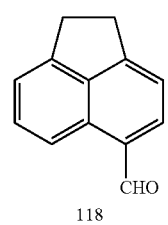
118

TABLE 2-continued
The Styryl Dye Library Decoding Table
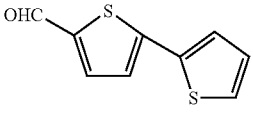
119
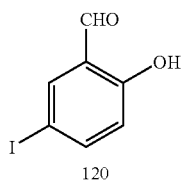
120
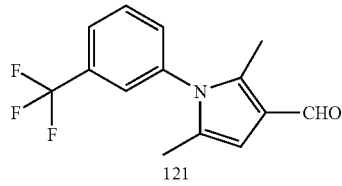
121
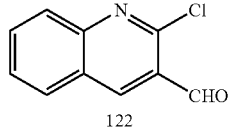
122
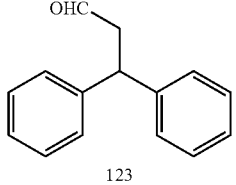
123
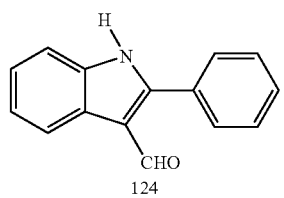
124
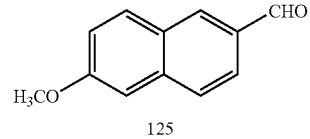
125
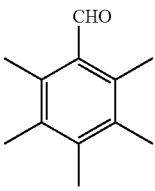
126
TABLE 2-continued
The Styryl Dye Library Decoding Table
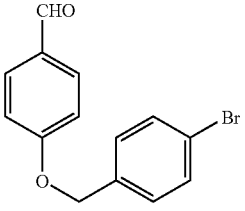
127
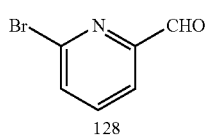
128
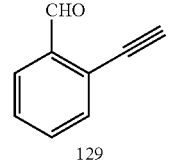
129
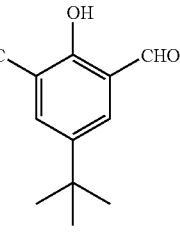
130
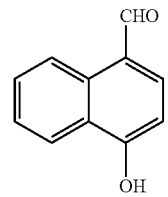
131
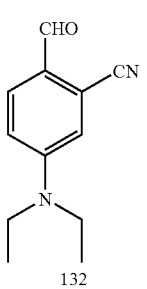
132
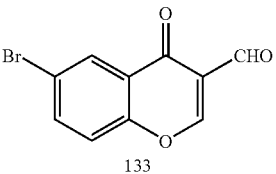
133

TABLE 2-continued

The Styryl Dye Library Decoding Table 134
135
136
137
138
139
140
141
142
143
144
145
146
147
148
149

TABLE 2-continued
The Styryl Dye Library Decoding Table
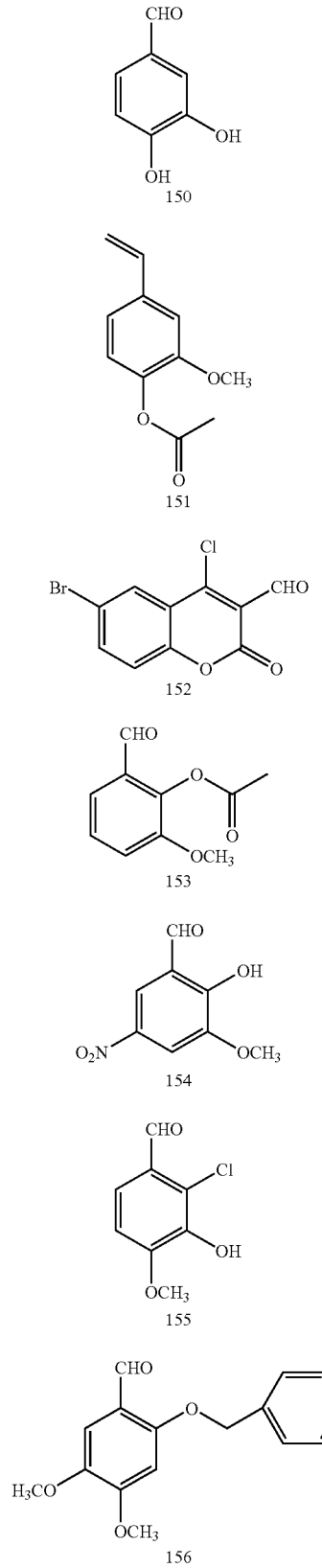
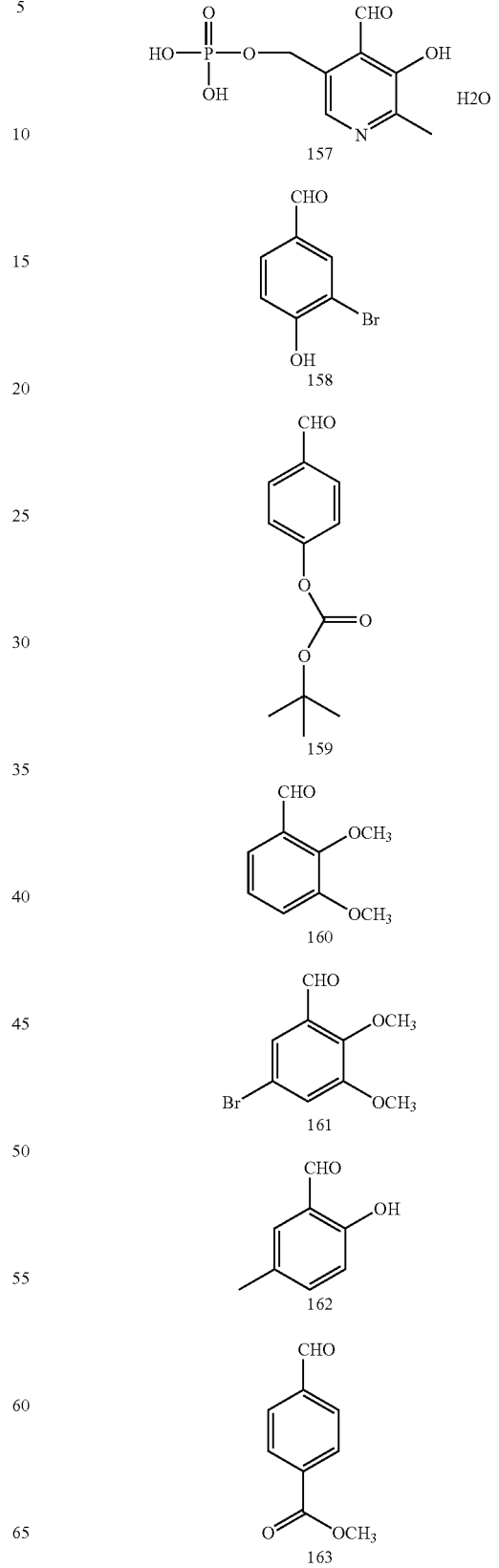

TABLE 2-continued

The Styryl Dye Library Decoding Table

164: 3,4-dichlorobenzaldehyde structure (CHO with two Cl)

165: 3,5-di-tert-butyl-2-hydroxybenzaldehyde structure (CHO, OH, two tert-butyl)

166: benzaldehyde with two Cl, OH, and OCH₃ substituents

167: furan-based aldehyde with acetate ester

168: 2,3-dihydroxybenzaldehyde

Example 14

Primary and Secondary Screening

Figure 2:
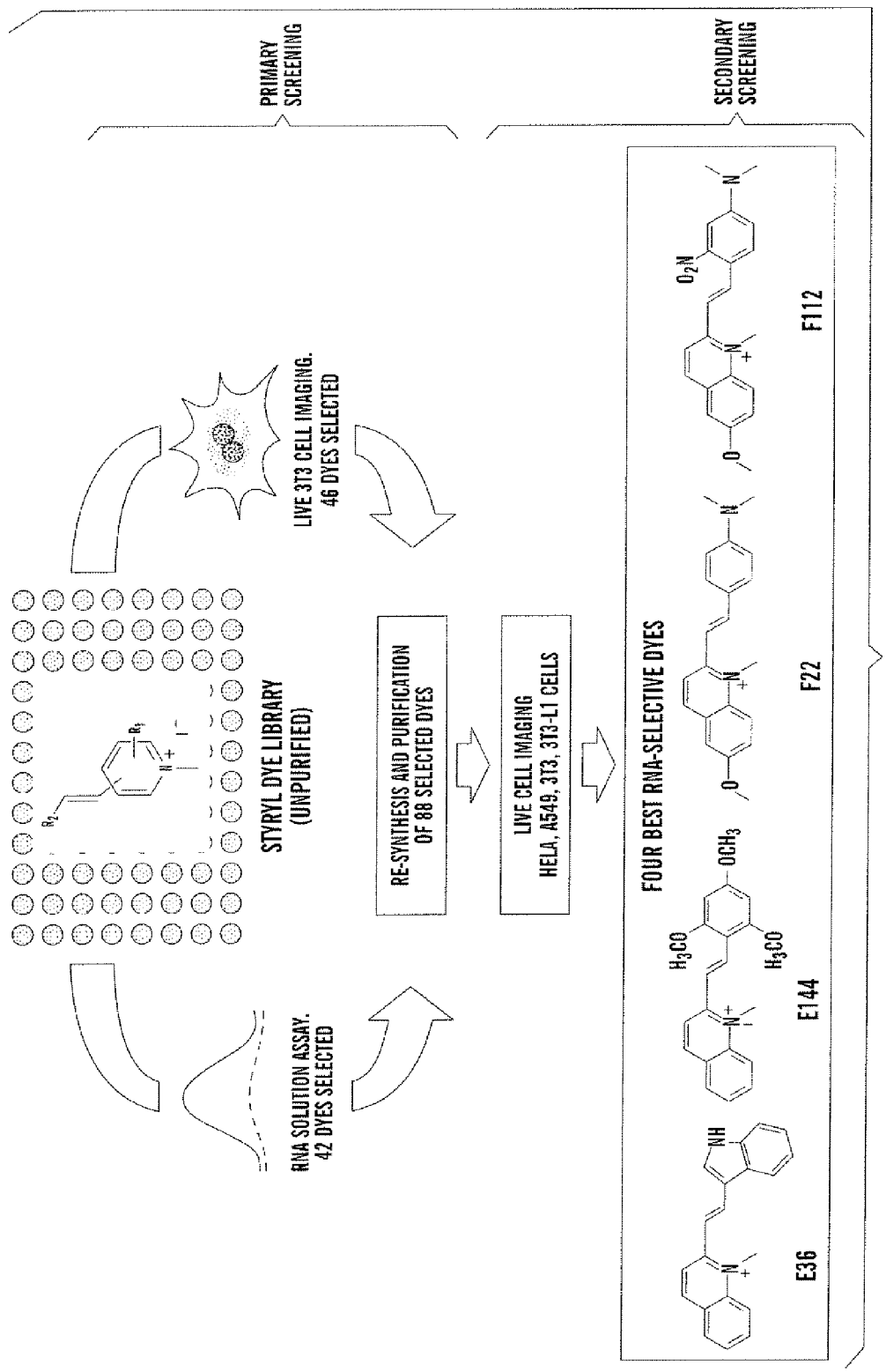
FIG. 2 illustrates the screening strategy used to identify novel compounds.

The screening strategy used in this study is illustrated in FIG. 2. Both in vitro RNA assays and live cell imaging methods were utilized in the primary screening of the dye library. Selective binding of the dye to RNA in solution was the primary criterion for selecting lead compounds for subsequent bioimaging studies, Herein, the library dyes' fluorescent emission intensity fold change upon binding to RNA was measured in solution. Dyes showing five-fold or higher emission changes in the presence of RNA were selected (Table 3). Note the dyes listed are identified by the building blocks I and II from Table 2. For example, A4 is the product made by reacting compound A from the list of Building block I and compound 4 from the list of Building block II.

TABLE 3

In Vitro Solution Assay Test of the Selected 42 Dye Compounds[a]

| Dye | Ex(nm) | Em(nm) | Fold[b] | Dye | Ex | Em | Fold |
|---|---|---|---|---|---|---|---|
| A4 | 450 | 540 | 11 | E105 | 450 | 550 | 39 |
| F4 | 450 | 560 | 62 | F105 | 450 | 550 | 101 |
| A8 | 450 | 580 | 37 | D107 | 500 | 620 | 13 |
| C8 | 450 | 570 | 9 | E107 | 500 | 610 | 10 |
| F8 | 500 | 610 | 52 | A108 | 450 | 590 | 8 |
| A9 | 500 | 600 | 21 | C108 | 450 | 580 | 8 |
| C9 | 500 | 610 | 9 | D108 | 500 | 630 | 21 |
| F9 | 500 | 620 | 86 | E108 | 500 | 620 | 21 |
| G9 | 500 | 620 | 16 | F108 | 500 | 610 | 27 |
| A10 | 500 | 610 | 23 | E111 | 500 | 620 | 17 |
| F10 | 500 | 630 | 38 | A121 | 450 | 540 | 28 |
| A22 | 500 | 610 | 28 | D121 | 500 | 600 | 41 |
| C22 | 500 | 630 | 6 | C125 | 450 | 580 | 6 |
| F22 | 500 | 640 | 23 | A132 | 500 | 610 | 17 |
| A24 | 500 | 660 | 103 | B132 | 500 | 590 | 28 |
| A42 | 450 | 560 | 10 | F132 | 500 | 640 | 14 |
| E43 | 450 | 560 | 10 | A144 | 450 | 530 | 26 |
| B92 | 500 | 600 | 28 | E144 | 450 | 540 | 5 |
| C92 | 500 | 630 | 15 | A156 | 450 | 580 | 42 |
| F92 | 500 | 640 | 20 | B156 | 450 | 560 | 54 |
| D105 | 450 | 590 | 16 | F158 | 500 | 620 | 7 |

[a] Dye final concentration was 10 μM. RNA (Type VI from torula yeast) solution concentration was 500 μg/mL in TE buffer.
[b] Represents the compound's fluorescent emission fold changes to RNA.

The entire library was also screened directly by live cell imaging using 3T3 fibroblast cells in a 50 μM concentration. A total of 46 dyes were identified based on selective localization of the fluorescent signal to cell nucleoli as well as high signal intensity and low photobleaching (see Table 4).

TABLE 4

46 Dye Compounds Selected From Live Cell Imaging in the Primary Screening[a]

| Dye | SPECTRUM EX | SPECTRUM EM | Dye | SPECTRUM EX | SPECTRUM EM |
|---|---|---|---|---|---|
| F40 | 400 | 490 | F119 | 500 | 610 |
| F41 | 450 | 590 | F120 | 450 | 550 |
| F43 | 450 | 560 | F121 | 450 | 550 |
| F44 | 450 | 570 | F123 | 450 | 530 |
| F45 | 400 | 490 | F128 | 400 | 510 |
| F47 | 350 | 470 | F137 | 400 | 540 |
| F48 | 400 | 480 | F138 | 350 | 460 |
| F73 | 400 | 490 | F141 | 450 | 560 |
| F74 | 450 | 550 | F143 | 450 | 550 |
| F75 | 400 | 510 | F145 | 400 | 540 |
| F77 | 350 | 440 | F153 | 350 | 470 |
| F82 | 400 | 490 | F155 | 450 | 540 |
| F83 | 350 | 460 | F158 | 500 | 620 |
| F85 | 400 | 470 | E36 | 450 | 550 |
| F97 | 350 | 460 | E63 | 400 | 480 |
| F101 | 350 | 470 | E73 | 450 | 550 |
| F104 | 350 | 460 | E83 | 350 | 450 |
| F105 | 450 | 550 | E77 | 350 | 470 |
| F112 | 500 | 620 | E119 | 450 | 600 |
| F114 | 400 | 490 | D84 | 350 | 460 |
| F115 | 500 | 650 | D143 | 400 | 530 |
| F116 | 400 | 520 | A158 | 450 | 580 |
| F118 | 450 | 590 | B139 | 450 | 570 |

[a] Dye concentration was 10 μM in TE buffer

The selected compounds from both primary screens (total 88) were resynthesized in large scale and purified. The compounds' live cell nuclear imaging properties were then tested by four cell lines, including two mouse cell lines: 3T3 fibroblast cells and 3T3-L1 adipocyte cells; and two human cancer cell lines: Hela cells and A549 human lung carcinoma cells. Herein, the final dye concentration in each test was decreased to 25 µM and all the experiments were repeated to establish reproducibility. From this secondary screening, the four best compounds (E36, E144 F112, and F22) were finally selected based on their selective nucleolar targeting, high fluorescence intensity, low photobleaching, and low cellular toxicity. Each of the three dyes contained at least one high affinity nucleic acid functional group (Trotta et al., "Solution Structure of DAPI Selectively Bound in the Minor Groove of a DNA T-T Mismatch-Containing Site: NMR and Molecular Dynamics Studies," *Nucleic Acids Res.* 26:4706-4713 (1998); Loontiens et al., "Binding Characteristics of Hoechst 33258 with Calf Thymus DNA, Poly[d(A-T)], and d(CCGGAATTCCGG): Multiple Stoichiometries and Determination of Tight Binding with a Wide Spectrum of Site Affinities," *Biochem.* 29:9029-9039 (1990); Zipper et al., "Investigations on DNA Intercalation and Surface Binding by SYBR Green I, Its Structure Determination and Methodological Implications," *Nucleic Acid Res.* 32:E103 (2004); Glazer et al., "Stable Dye-DNA Intercalation Complexes as Reagents for High-Sensitivity Fluorescence Detection," *Nature* 359:859-861 (1992), which are hereby incorporated by reference in their entirety) in building block II such as the terminal secondary amine for F22 and F112, the trimethoxy for E 144, and the indole for E36. Each compound also contained a quinaldine or 6-methoxy quinaldine moiety, suggesting the quinaldine group may be important in live cell RNA structure targeting and cell permeability.

Example 15

RNA Response in Solution

The detailed fluorescent properties of three selected dyes including; excitation/emission $\mu_{max}$, the quantum yield and extinction coefficient of both free dye solution and dye-RNA solution were assessed (Table 5). All three dyes showed a significant quantum yield increase in RNA solution. Moreover, all of the dyes' excitation $\lambda_{max}$ showed a clear red shift (16 to 56 nm) in the presence of RNA, while the emission $\lambda_{max}$ stayed similar.

TABLE 5

Three Selected Dyes Chemistry Structure, their Solution Fluorescent Response to RNA and Optimum Concentration for Live Cell Imaging

| Dye | Structure | EX/EM[a] (nm) Buffer | (nm) RNA | $\Phi_F^{free,b}$ | $\Phi_F^{RNA}$ | $\Phi_F^{RNA}/\Phi_F^{free}$ | $\epsilon^{free}$ (M$^{-1}$cm$^{-1}$)[c] | $\epsilon^{RNA}$ (M$^{-1}$cm$^{-1}$) | Optimum Concentration |
|---|---|---|---|---|---|---|---|---|---|
| E36 | 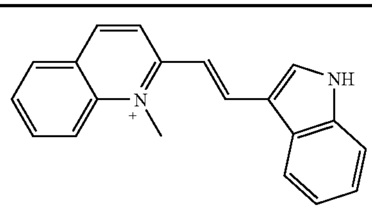 | 457/541 | 497/548 | 0.0019 | 0.1041 | 54.6 | 3.94 × 10$^4$ | 4.31 × 10$^4$ | 5 µM |
| E144 | 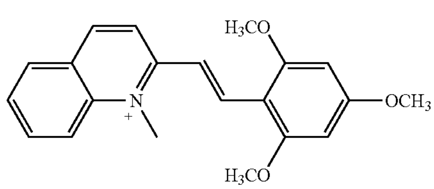 | 440/532 | 456/532 | 0.0056 | 0.0310 | 5.5 | 1.32 × 10$^4$ | 1.46 × 10$^4$ | 5 µM |
| F22 | 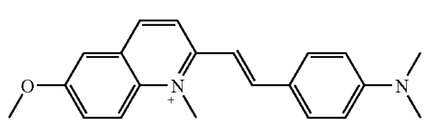 | 492/598 | 548/620 | 0.0007 | 0.0075 | 10.7 | 1.74 × 10$^4$ | 2.00 × 10$^4$ | 5 µM[d] |
| F112 | 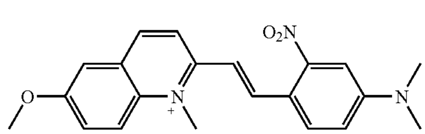 | 462/516 | 465/514 | | | | | | 10 µM |

[a]Excitation and emission $\lambda_{max}$(nm) of three selected dyes obtained by Hitachi F-2500 FL fluorophotometer in TE buffer, pH = 7.5. Dye final concentration was 5 µM and RNA (16S- and 23S-ribosomal from *E. coli*) solution final concentration was 200 µg/mL.
[b]Quantum yield measured by Gemini XS fluorescent plate reader in TE buffer, pH = 7.5. Rhodamine 6G 5 µM aqueous solution was used as standard. Dye final concentration was 5 µM for E36 and 10 µM for E144 and F22. RNA solution final concentration was 200 µg/mL.
[c]Extinction coefficient measured by SpectraMax Plus384 absorbance plate reader. Solution condition was same as quantum yield measurement.
[d]3T3 cells could be imaged at 1 µM concentration.

Figure 3A:
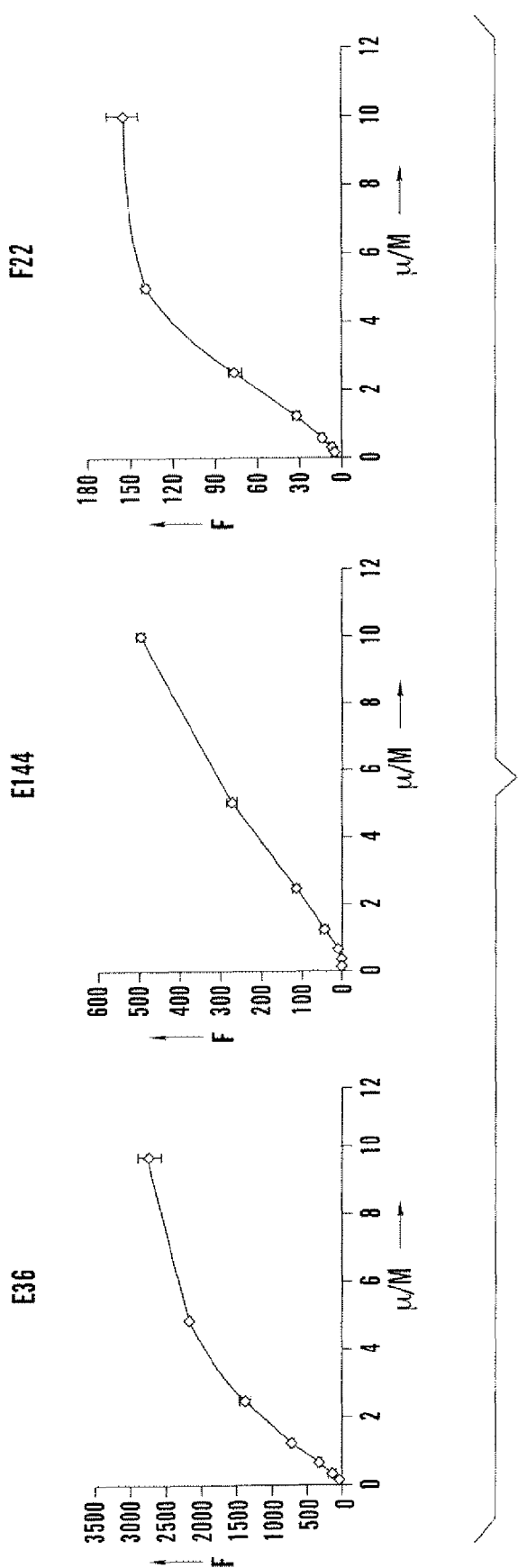
FIG. 3A-B shows the RNA and DNA response in solution of selected dyes.

The RNA binding characteristics of these dyes was further examined by determining if the fluorescent intensity was concentration dependent (FIG. 3A). In the tested concentration range (0.15 μM to 10 μM for dye, 50 μg/mL for RNA), an obvious intensity increase was observed in the three dyes tested. An almost linear curve was obtained in the titration of E144, while E36 and F22 both showed evidence of saturation at high concentration. Moreover, a slight emission Ma red shift was observed (total 8 nm) with the increasing concentration of E36. This may suggest a stacking binding mode of this dye to RNA backbone (Sovenyhazy et al., "Spectroscopic Studies of the Multiple Binding Modes of a Trimethine-Bridged Cyanine Dye with DNA," *Nucleic Acid Res.* 31:2561-2569 (2003), which is hereby incorporated by reference in its entirety). Compounds E144 and F22 did not show obvious wavelength shift upon increasing dye concentrations.

Example 16

Optimization of Working Concentration and Imaging Properties

Figure 4:
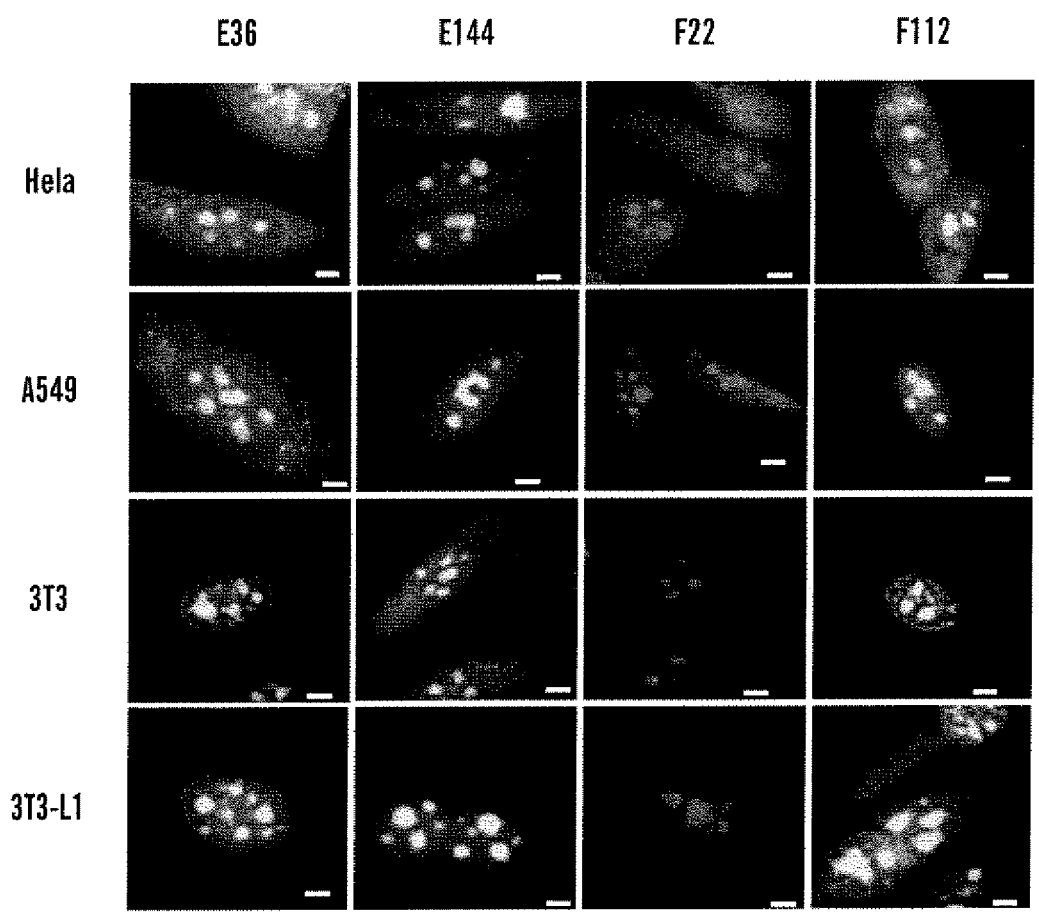
FIG. 4 shows live cell RNA staining using selected dyes E36, E144, and F22 at 5 µM and F112 at 10 µM concentration. The picture of F22 stained 3T3 cells was obtained in 1 µM dye concentration. 1000× magnification was utilized in imaging. Scale bar represents 5 micrometer. Image brightness and contrast were slightly adjusted to improve picture quality. E36, E144, F112 (Green: FITC channel), F22 (Red: Cy3 channel).

In fluorescence microscopic imaging studies, it is always desirable to use as little dye as possible to stain organelles in order to maximize specificity and minimize dye toxicity and cell death. To determine the lowest working concentration of each dye, four different concentrations (20 μM, 10 μM, 5 μM, and 1 μM) were tested in four cell lines (Hela, A549, 3T3, and 3T3-L1). Dyes E36, E144, and F112 were imaged using FITC channel, and F22 was imaged using Cy3 channel. Generally, a quality fluorescence signal for each dye was produced using a concentration of 5 μM for E36, E144, and F22 and 10 μM for F112 (Table 5). It was interesting to observe that compound F22 was brighter in 3T3 cells, and a concentration of 1 μM was sufficient for a clear image (FIG. 4). The compounds showed distinguishable clear nucleolar staining with faint nuclear and cytoplasmic staining in each cell line tested. Little photobleaching and no obvious cell morphology or viability changes were observed during the tests.

Live cell staining by SYTO®RNASelect had been reported recently (Santangelo et al., "Live-Cell Characterization and Analysis of a Clinical Isolate of Bovine Respiratory Syncytial Virus, Using Molecular Beacons," *J. Virol.* 80:682-688 (2006), which is hereby incorporated by reference in its entirety). Unfortunately, in this report, the staining of live cell RNA was mainly in the cytoplasm with little staining in the nucleus. A similar result was observed in the current study when using SYTO®RNASelect for the four cell lines following the experimental protocol provided by the company. Therefore, although SYTO®RNASelect does stain fixed cell nucleoli (Haulgland, "The Handbook, A Guide to Fluorescent Probes and Labeling Technologies," tenth ed. M. T. Z. Spence, eds. pp 327, 710-711; Voss et al., "Effect of Mutation of Amino Acids 246-251 (KRKHKK) in HSP72 on Protein Synthesis and Recovery From Hypoxic Injury," *Am. J. Physiol. Heart Circ. Physiol.* 289:H2519-H2525 (2005), which are hereby incorporated by reference in their entirety), it may not be good for live cell nucleolar RNA imaging applications. Clearly, the RNA-selective dyes reported in this study surpassed commercially-available RNA probes in terms of their usefulness in live cell imaging experiments.

Example 17

Dye Cell-Tolerability

Low cytotoxicity is one of the most important criteria for live cell imaging probes. All four compounds were tested at 20 μM, 10 μM, 5 μM, and 1 μM in Hela, A549, 3T3, and 3T3-L1 cells. Cell viability and morphology changes were observed during 2, 8, and 24 hours. Only dye E36 was toxic to A549, 3T3, and 3T3-L1 cells at high concentration (20 μM) after 8 hours.

Figure 5A:
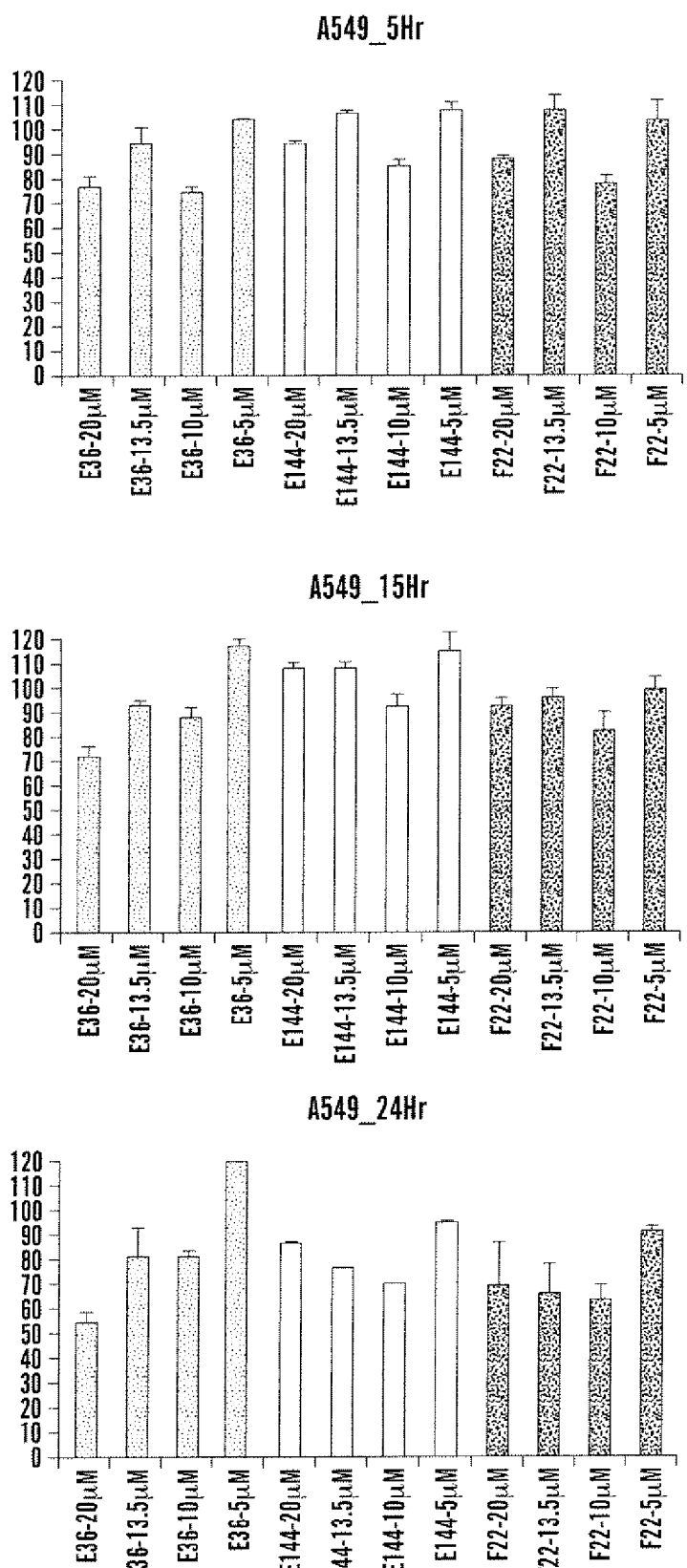
FIG. 5A-B shows the cytotoxicity and phototoxicity associated with the selected dyes.
Figure 5A:
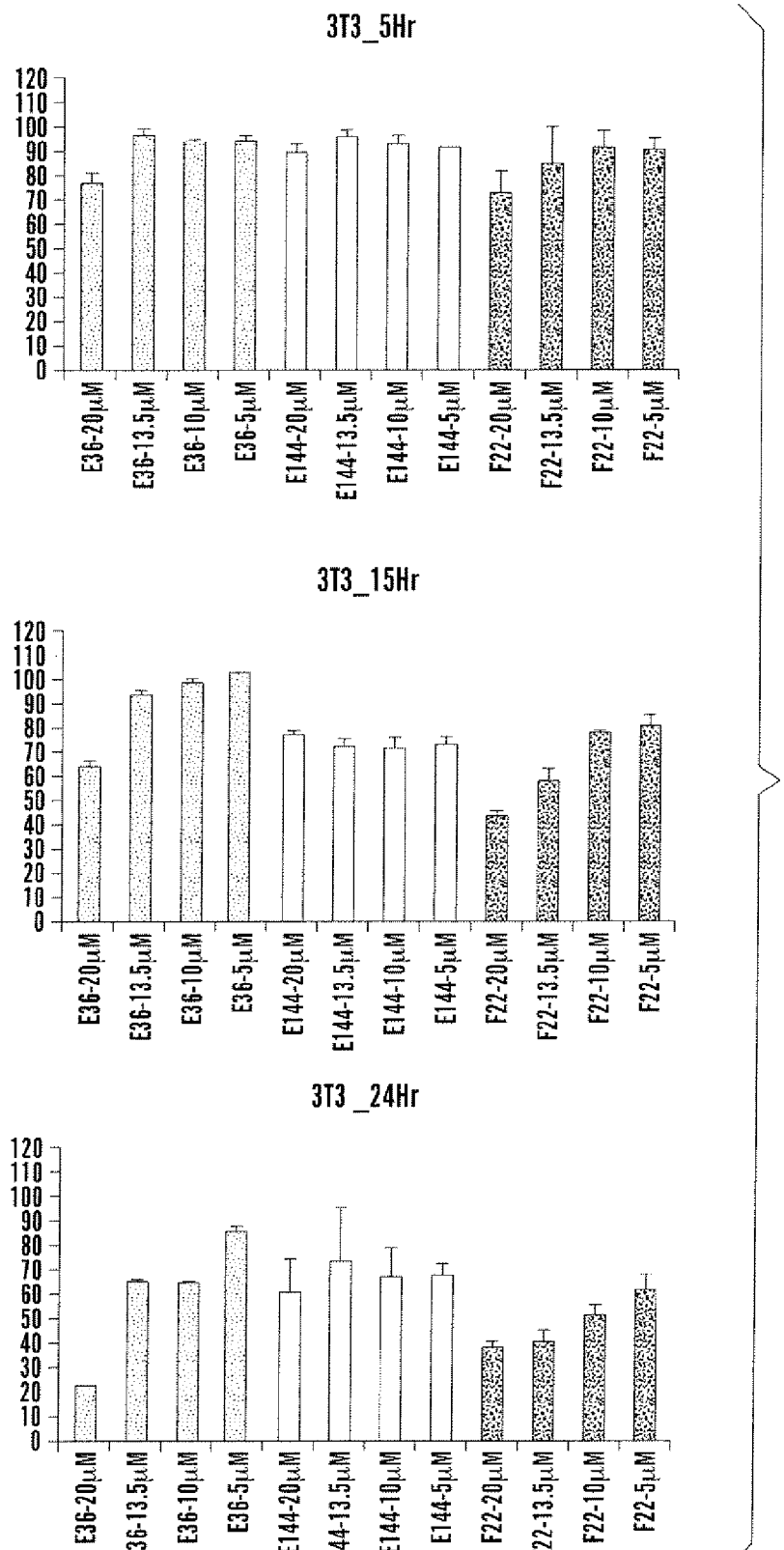

In addition, E36, P144, and F22 were tested in four concentrations (20 μM, 13.5 μM, 10 μM, and 5 μM) in A549 and 3T3 cells and the cytotoxicity was measured using standard MTS assay after 5, 15, or 24 hours incubation (FIG. 5A). Generally, there was no toxicity (defined by greater than 50% cell death) associated with any of the dyes at the working concentration (5 μM) after 24 hours incubation. In A549 cell, all three dyes were non-toxic after 24 hours incubation at all concentrations. In 3T3 cells, E144 was non-toxic, but 20 μM of E36 was toxic after 24 hours incubation and 20 μM F22 was toxic after 15 hours incubation. Since the compounds bind to RNA, it is not surprising to see some signs of toxicity at higher concentrations, especially after one doubling period (approximately 22 hours for A549 cells and 20-25 hours for 3T3 cells). Fortunately, toxicity was only apparent at high concentrations after long incubation times and minimal to no toxicity was observed at the lower, working concentrations of the compounds. This data demonstrates the applicability of these dyes as probes for imaging RNA distribution within live cells. Additional studies are required to determine if the compounds perturb nucleolar dynamics throughout the cells cycle.

Figure 5B:
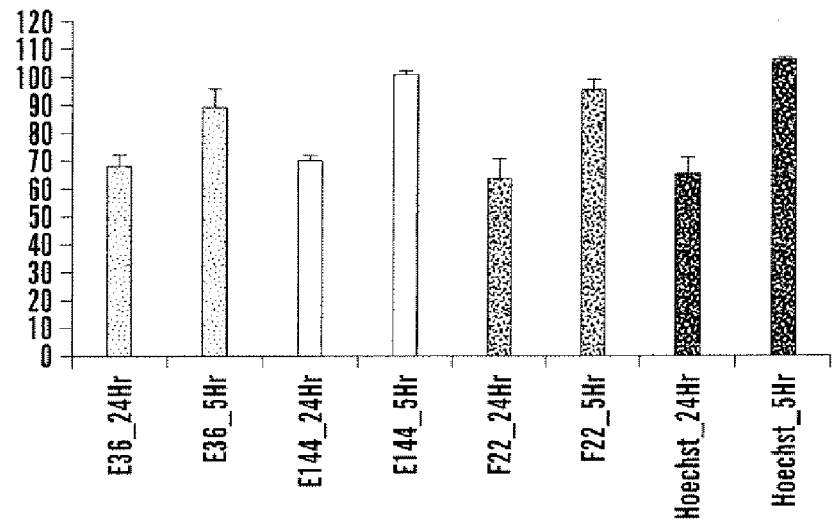
Figure 5B:
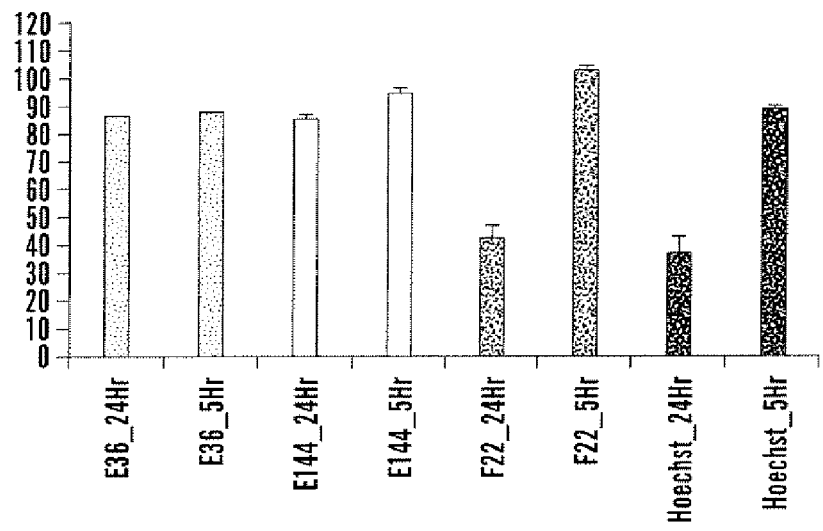

Phototoxicity is also an important factor in evaluating applicability of new fluorescent probes for live cell imaging. Phototoxicity is predominantly caused by the direct absorption of high energy UV light by the chromophores or by the generation of singlet oxygen due to the non-radiative energy transfer. Dyes that are excited by high energy (violet-UV) wavelength light (such as Hoechst (Libbus et al., "Incidence of Chromosome Aberrations in Mammalian Sperm Stained with Hoechst 33342 and UV-Laser Irradiated During Flow Sorting," *Mutat. Res.* 182.265-270 (1987), which is hereby incorporated by reference in its entirety)) are most often prone to phototoxicity, although even longer wavelength dyes (such as FITC (Rumbaut et al., "Differential Phototoxicity of Fluorescent Dye-Labeled Albumin Conjugates," *Microcirculation* 6:205-213 (1999), which is hereby incorporated by reference in its entirety) and Rhodamine (Shea et al., "Rhodamine 123 Phototoxicity in Laser-Irradiated MGH-U1 Human Carcinoma Cells Studied In Vitro by Electron Microscopy and Confocal Laser Scanning Microscopy," *Cancer Res.* 50:4167-4172 (1990), which is hereby incorporated by reference in its entirety)) also exhibit light-induced toxicity if irradiated for prolonged periods of time. Nevertheless, it is desirable for the new imaging probes to be as non-phototoxic as possible. To investigate the phototoxicity of the present RNA-selective compounds, cellular viability of irradiated cells using MTS assay was assessed. Cells were incubated with dyes (E36, E144, and F22) in their working concentration (5 µM), and then irradiated with the appropriate filters using the fluorescent microscope (FITC for E36 and E144; Cy3 for F22). While light exposures used for imaging experiments are generally a few seconds long at most, cells were irradiated for 5 minutes for prolonged toxicity measurement. Irradiated cells were then incubated for 5 and 24 hours before tested by MTS assay. Both the cancer cell line (A549) and normal cell line (3T3) were tested in parallel (FIG. 5B). In general, the toxicity was minimal. F22 was phototoxic in 3T3 cells only (not A549) after 24 hours incubation, but this effect was negligible at 5 hours incubation. For comparison, Hoechst 33258 was tested and found to be as toxic in 3T3 cells as F22 after 24 hours incubation. Therefore, phototoxicity of the present RNA-selective compounds is comparable to and even lower than that of Hoechst—a broadly-used, live cell DNA imaging probe.

Example 18

RNA vs. DNA Specificity

Figure 3B:
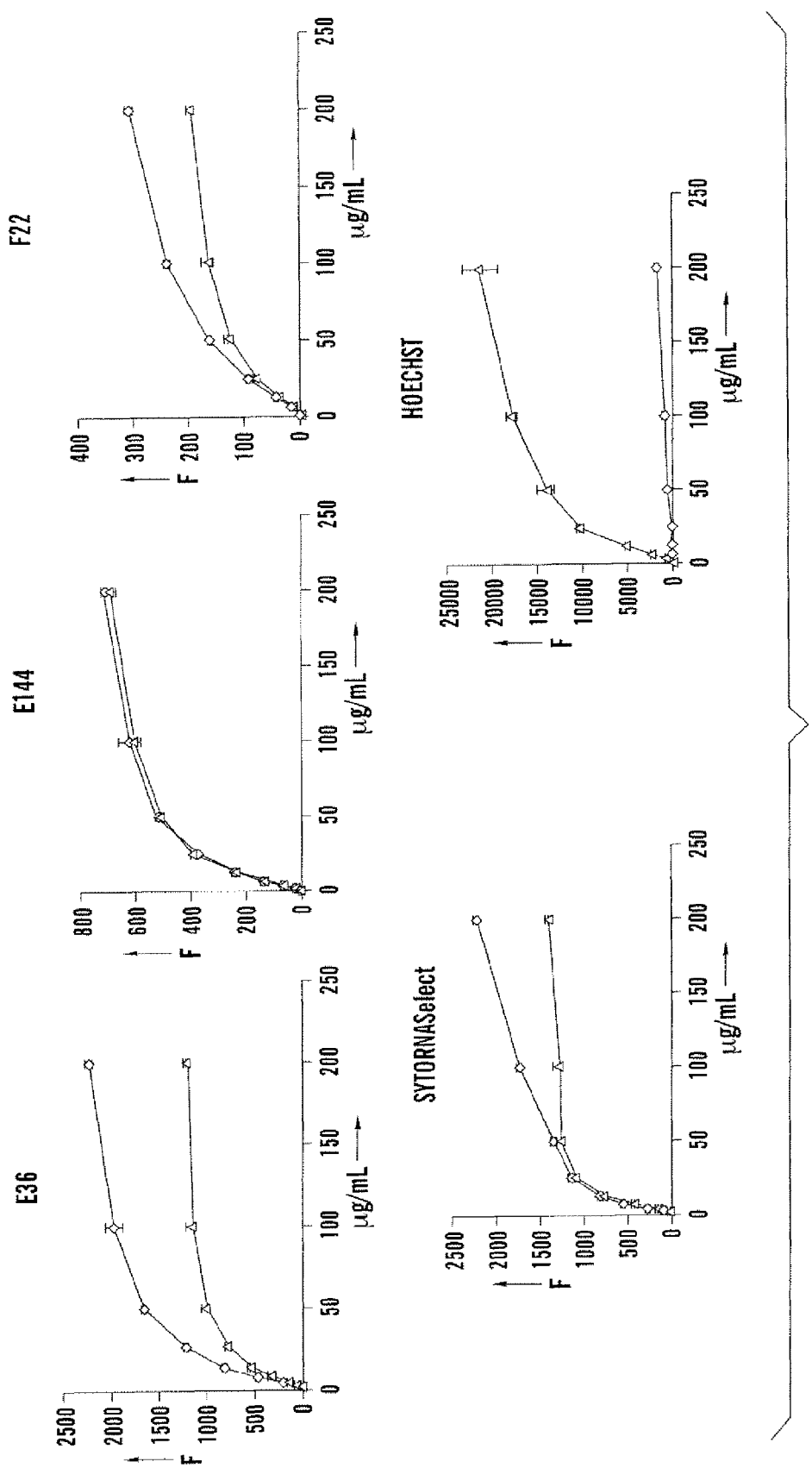

A set of solution assay experiments were then carried out to investigate the dyes' selectivity to bind RNA vs. DNA in vitro. With a fixed concentration of dye (E36 5 µM, E144 10 µM, and F22 10 µM), the fluorescent intensity at various nucleic acid concentrations (0.195 µg/mL to 200 µg/mL) was determined at the appropriate emission $\lambda_{max}$ wavelength. SYTO®RNASelect (5 µM) and Hoechst 33258 (5 µM) dyes were used as standards for RNA selective and DNA selective dyes (FIG. 3B). When plotting the intensity changes with the increasing concentration of RNA or DNA, both E36 and F22 showed a higher response to RNA than to DNA which corresponds to better nucleoli targeting in live cells. The RNA selectivity of these dyes was comparable or higher than commercial SYTO®RNASelect. E144, however, showed almost same binding affinity to both RNA and DNA.

Figure 6:
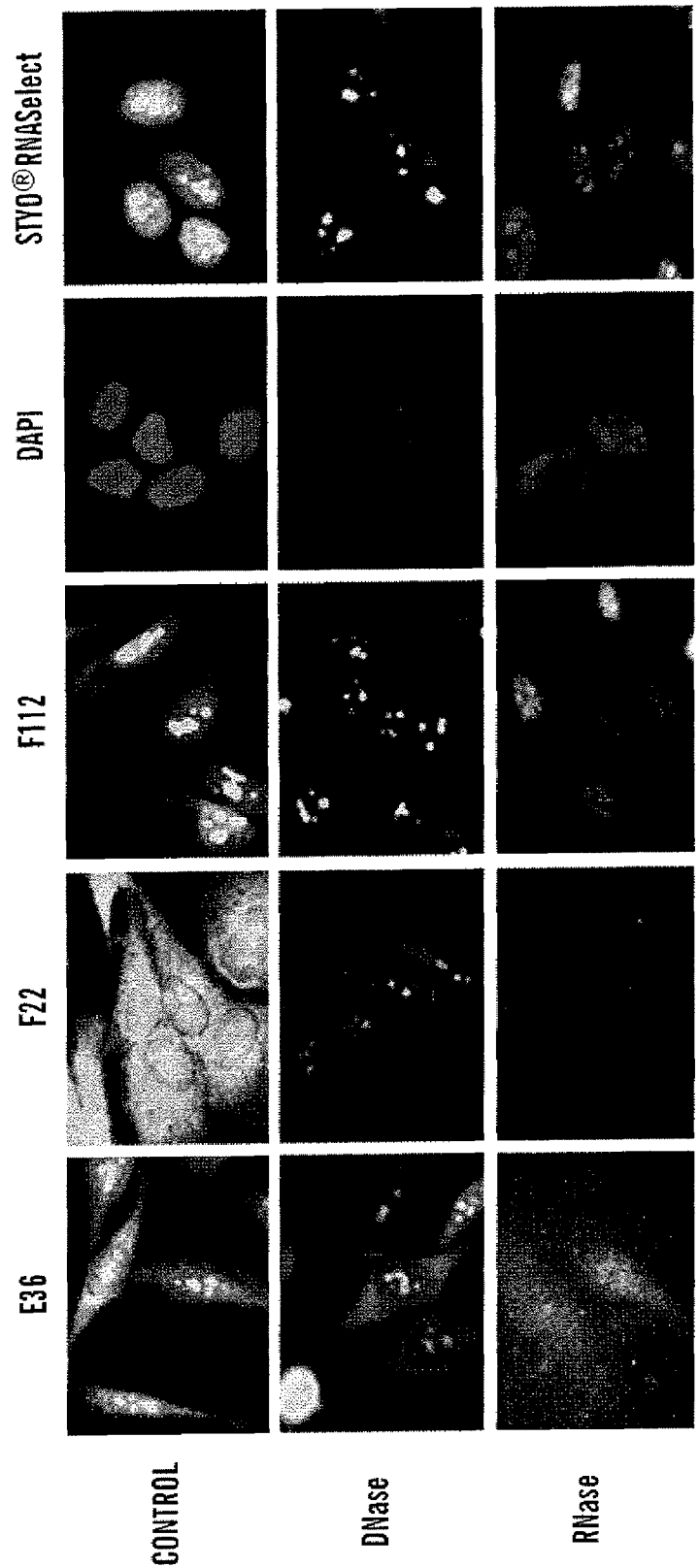
FIG. 6 shows the images of fixed-permeabilized Hela cells stained with E36, F112, F22, DAPI, or SYTO®RNASelect. Equal exposure was used for the same dye imaging after DNase or RNase treatment. E36, F112, and F22 were tested at 50 µM. DAPI was tested at 10 µM and SYTO®RNASelect was tested at 5 µM. 1000× magnification was utilized in the imaging. Scale bar represents 5 micrometer. Brightness and contrast of control and DNase images of F22 were adjusted to improve picture quality. DAPI (Blue: DAPI channel), E36 and SYTO®RNASelect (Green; FITC channel), F22 (Red: Cy3 channel).

To further confirm that the compounds selectively bind RNA, a deoxyribonuclease (DNase) and ribonuclease (RNase) digest test was performed. In DNase digest, only the DNAs in the cell would be hydrolyzed. By contrast, in RNase digest, only RNAs would be hydrolyzed. Fixed-permeabilized Hela cells were used in this experiment and DAPI and SYTO®RNASelect were used as control dyes (FIG. 6). As expected, the fluorescence of compound E36 dramatically diminished in cells following the RNase digest. However following DNase treatment, the nucleolar fluorescence intensity stayed almost the same as it was without treatment. Dye F112 showed almost the same pattern as SYTO®RNASelect. It also left a slight stain of the nucleus after RNase treatment, while bright nucleolar staining remained after DNase treatment. Compound F22 showed an overall decrease in intensity following both DNase and RNase treatments; however, the nucleolar stain remained bright after the DNase treatment. The selective staining of dye E144 was not detectable after DNase and RNase experiments. It was observed that a dramatic decrease in fluorescence in E144 was also induced by permeabilization process itself, which means that the detergent, Triton X-100, may interfere with the binding affinity of E144 to cellular nucleic acids. Still, its higher RNA-selective binding in live cell might be due to the complicated in vivo live cell environment, which may preferably direct this dye to nucleoli. In short, although it is practically impossible to develop a compound that is 100% specific for RNA binding, the DNase and RNase experiments clearly demonstrate that the selectivity of the present compounds is outstanding.

Example 19

Figure 7:
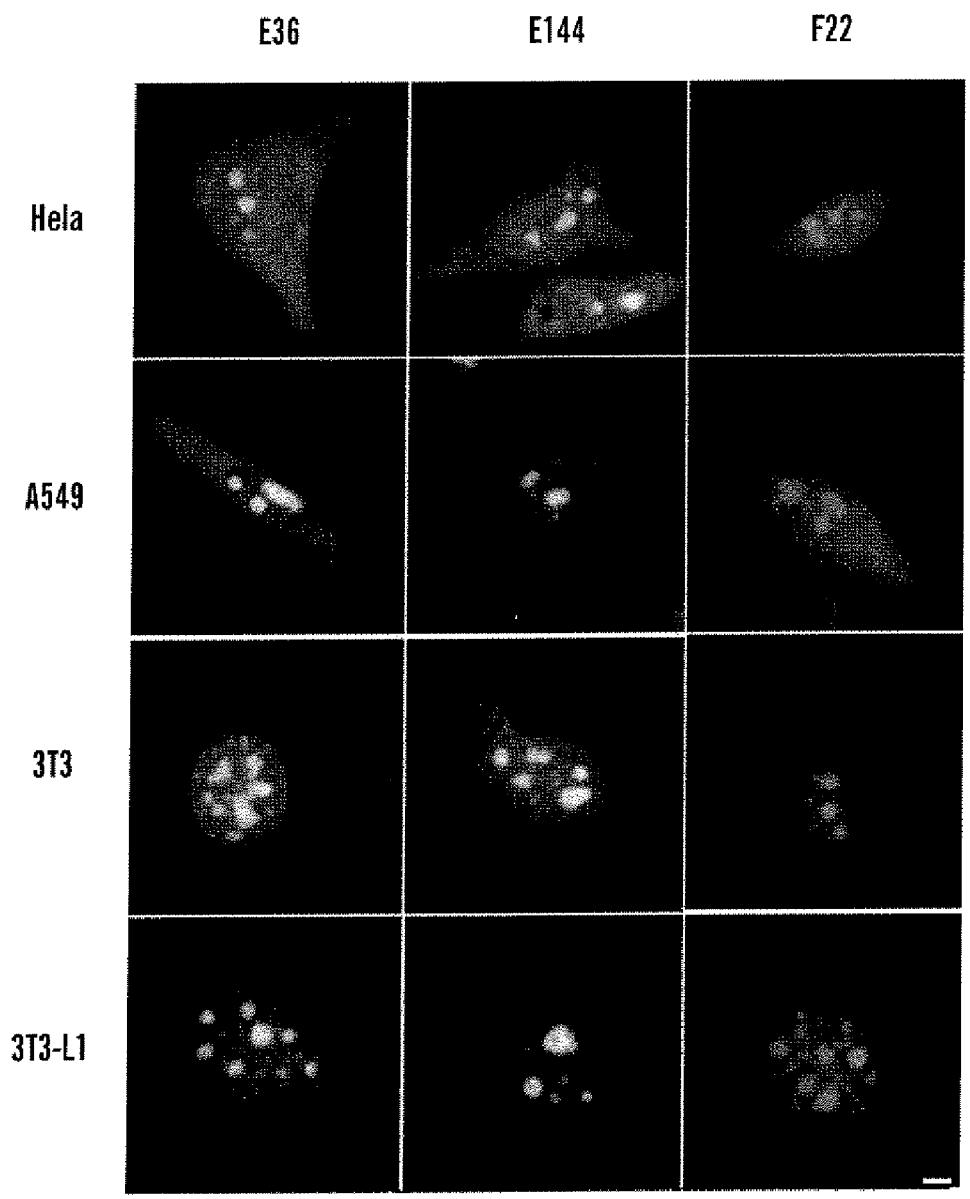
FIG. 7 shows live cell dual localization of RNA and DNA in Hela, A549, 3T3, and 3T3L1 cells using E36 (5 µM), E144 (5 µM), or F22 (1 µM), in combination with Hoechst (1 µM). 100× magnification was utilized in the imaging. Scale bar represents 5 micrometer. Image brightness and contrast were adjusted to improve picture quality. E36, E144 (Green: FITC channel), F22 (Red. Cy3 channel), Hoechst (Blue: DAPI channel).
Figure 8:
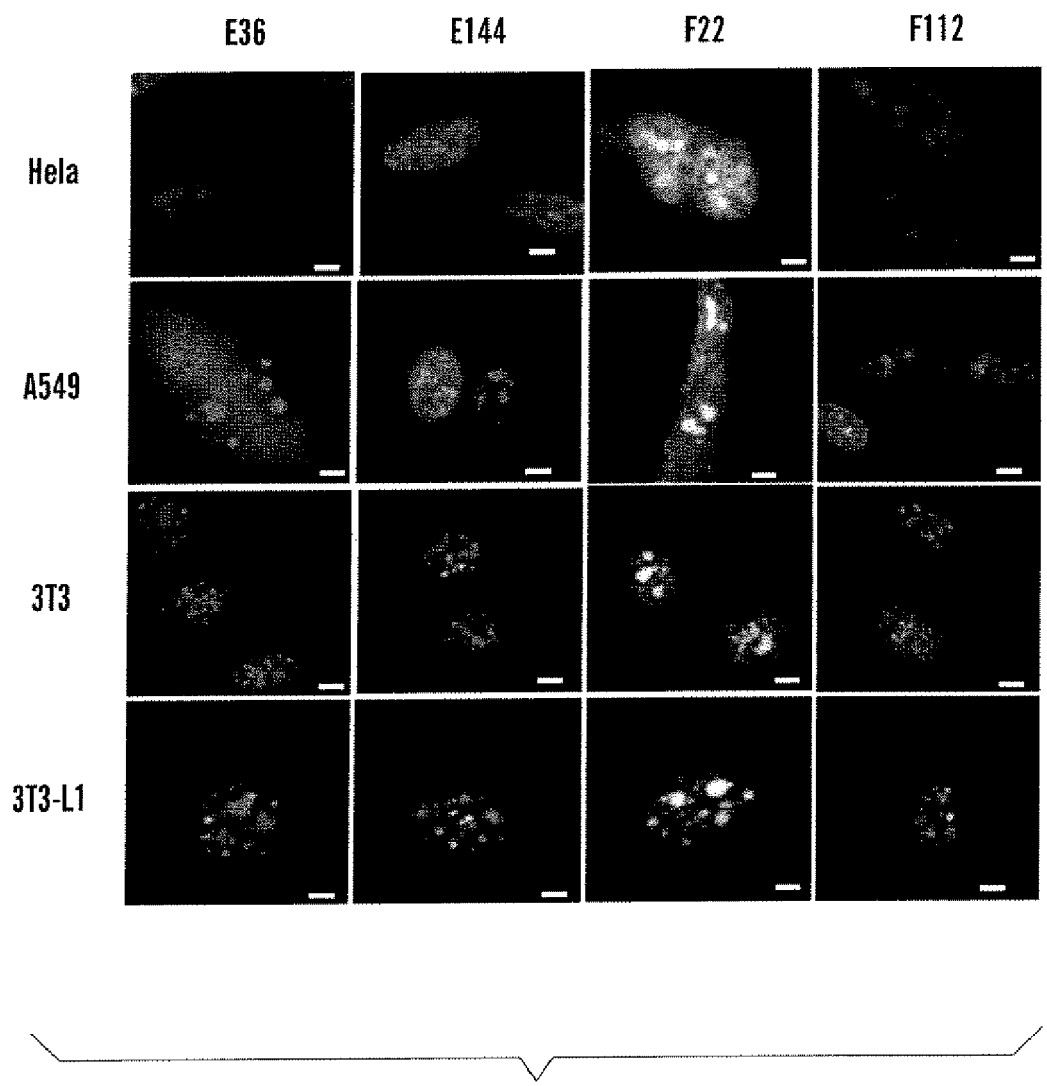
FIG. 8 shows live cell dual localization of RNA and DNA in Hela, A549, 3T3, and 3T3L1 cells using E36 (5 µM), E144 (5 µM), F22 (1 µM), or F112 (10 µM) in combination with DAPI (1 µM). 1000× magnification was utilized in the imaging. Scale bar represents 5 micrometer. Image brightness and contrast were adjusted to improve picture quality. E36, E144, F112 (Green: FITC channel), F22 (Red: Cy3 channel), DAPI (Blue. DAPI channel).

Counterstain Compatibility to Hoechst/DAPI and Determining Higher Order Nuclear Organization To study the higher order nuclear organization of RNA molecules, cells stained with a RNA-selective dye need to be counter-labeled with a DNA-selective dye, such as Hoechst or DAPI. The classic live cell staining dyes, Hoechst and DAPI, have been widely used as DNA markers in the bioimaging field. The compounds of the present invention are highly compatible with Hoechst and DAPI stains making them suitable for dual imaging of DNA and RNA distribution. Dual staining of the RNA-selective compounds with Hoechst (FIG. 7) and DAPI (FIG. 8) was carried out using DAPI, FITC, and Cy3-specific excitation/emission filter sets. The blue nucleus stain was clearly visible in the DAPI channel as was the nucleolar stain in either the FITC or Cy3 channel.

To address whether higher order structural organization of the nucleus may be related to different patterns of transcriptional activity, the distribution of DNA and RNA molecules in different cell lines was compared. Remarkably, the distribution of RNA rich-foci in relation to DNA-rich foci was largely cell-type dependent. In 3T3-L1 cells, for example, DNA-rich foci were immediately juxtaposed to RNA-rich regions In 3T3 cells, DNA rich foci appeared to be randomly distributed with respect to RNA-rich regions. Lastly, in Hela and A549 cells, DNA seemed to be distributed throughout the cell nucleus, whereas RNA-foci still seemed to be as prominent and localized as that observed in 3T3-L1 and 3T3 cells. This observation points to significant cell-type specific differences in RNA distribution, in relation to the condensation state of chromatin in different regions of the nucleus. Thus, there are significant differences in higher order organization that become immediately apparent upon microscopic observation of cells dual-labeled with DNA and RNA-selective fluorescent probes.

E36, E144, F112, and F22 are four novel fluorescent styryl compounds that are highly specific, live cell RNA-staining molecules suitable for microscopic imaging and nuclear structural studies. These dyes show low cell cytotoxicity, low phototoxicity and high photostability. Their fluorescence excitation/emission is orthogonal to commercially-available DNA binding dyes, and they are suitable for DNA-RNA colocalization experiments. Compared to SYTO®RNASelect, these dyes are more photostable and selective, especially because of their clear ability to specifically stain RNA-rich foci within the live cell nucleus. In conclusion, these styryl dyes open a new window into live cell microscopic imaging studies of nuclear structure and function.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A fluorescent compound of the formula:

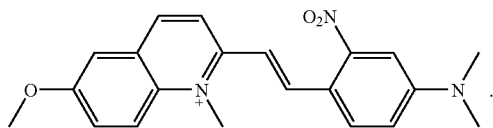

2. A process of making a product compound of the formula:

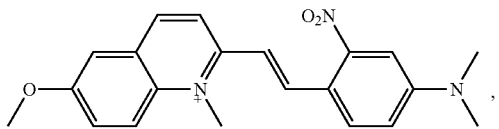

said process comprising:
reacting an aldehyde of the formula:

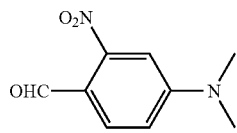

with a methylpyridinium salt of the formula:

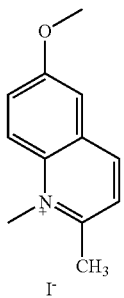

under conditions effective to produce the product compound.

3. The process according to claim 2, wherein said reacting is carried out in the presence of a secondary amine catalyst.

4. The process according to claim 2, wherein said reacting is cared out in the presence of exogenous energy.

5. The process according to claim 4, wherein the exogenous energy is microwave energy.

6. The process according to claim 2, wherein said reacting is carried out in a polar solvent.

* * * * *